US009938254B2

(12) United States Patent
Alexander et al.

(10) Patent No.: US 9,938,254 B2
(45) Date of Patent: Apr. 10, 2018

(54) ANTIPROLIFERATIVE COMPOUNDS, AND THEIR PHARMACEUTICAL COMPOSITIONS AND USES

(71) Applicant: Celgene Corporation, Summit, NJ (US)

(72) Inventors: Matthew D. Alexander, San Diego, CA (US); Matthew D. Correa, San Diego, CA (US); Joshua Hansen, La Jolla, CA (US); Raj Kumar Raheja, Poway, CA (US); John Sapienza, Chula Vista, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/400,208

(22) Filed: Jan. 6, 2017

(65) Prior Publication Data

US 2017/0197933 A1 Jul. 13, 2017

Related U.S. Application Data

(60) Provisional application No. 62/276,763, filed on Jan. 8, 2016.

(51) Int. Cl.
*C07D 401/04* (2006.01)
*C07F 9/59* (2006.01)
*A61K 31/454* (2006.01)
*A61K 31/675* (2006.01)

(52) U.S. Cl.
CPC .......... *C07D 401/04* (2013.01); *A61K 31/454* (2013.01); *A61K 31/675* (2013.01); *C07F 9/591* (2013.01)

(58) Field of Classification Search
CPC ..... C07D 401/04; C07F 9/591; A61K 31/454; A61K 31/675
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,328,245 A | 5/1982 | Yu et al. |
| 4,364,923 A | 12/1982 | Cook et al. |
| 4,409,239 A | 10/1983 | Yu et al. |
| 4,410,545 A | 10/1983 | Yu et al. |
| 4,414,209 A | 11/1983 | Cook et al. |
| 4,522,811 A | 6/1985 | Eppstein et al. |
| 4,810,643 A | 3/1989 | Souza |
| 4,994,443 A | 2/1991 | Folkman et al. |
| 4,999,291 A | 3/1991 | Souza |
| 5,001,116 A | 3/1991 | Folkman et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,229,496 A | 7/1993 | Deeley et al. |
| 5,323,907 A | 6/1994 | Kalvelage |
| 5,354,556 A | 10/1994 | Sparks et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,811,097 A | 9/1998 | Allison et al. |
| 5,840,674 A | 11/1998 | Yatvin et al. |
| 5,855,887 A | 1/1999 | Allison et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,893 A | 9/1999 | June et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |

(Continued)

FOREIGN PATENT DOCUMENTS

| WO | WO 2003/042402 A2 | 5/2003 |
| WO | WO 2008/156712 A1 | 12/2008 |

(Continued)

OTHER PUBLICATIONS

Anguille et al., "Leukemia-associated antigens and their relevance to the immunotherapy of acute myeloid leukemia," *Leukemia*, 26(10):2186-2196 (2012).
Brignone et al., "A soluble form of lymphocyte activation gene-3 (IMP321) induces activation of a large range of human effector cytotoxic cells," *J. Immunol.*, 179(6):4202-4211 (2007).
Buchwald et al., "Long-term, continuous intravenous heparin administration by an implantable infusion pump in ambulatory patients with recurrent venous thrombosis," *Surgery*, 88:507-516 (1980).
Carstensen, *Drug Stability: Principles & Practices*, Second Edition, Marcel Dekker, New York, NY, pp. 379-380 (1995).
Emens et al., "Chemotherapy: friend of foe to cancer vaccines," *Curr. Opin. Mol. Ther.*, 3(1):77-84 (2001).
Folkman et al., "Angiogenesis inhibition and tumor regression caused by heparin or a heparin fragment in the presence of cortisone," *Science*, 221:719-725 (1983).
Foster, "Deuterium isotope effects in the metabolism of drugs and xenobiotics: implications for drug design," *Adv. Drug Res.*, 14:1-40 (1985).

(Continued)

*Primary Examiner* — John M Mauro
(74) *Attorney, Agent, or Firm* — Jones Day

(57) ABSTRACT

Compounds of formula A-I and B-I, compositions comprising the compounds, methods of making the compounds and methods of their uses are disclosed.

33 Claims, No Drawings

(56) References Cited

U.S. PATENT DOCUMENTS

| | | | |
|---|---|---|---|
| 6,045,830 | A | 4/2000 | Igari et al. |
| 6,048,736 | A | 4/2000 | Kosak |
| 6,051,227 | A | 4/2000 | Allison et al. |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,207,157 | B1 | 3/2001 | Gu et al. |
| 6,248,363 | B1 | 6/2001 | Patel et al. |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,352,694 | B1 | 3/2002 | June et al. |
| 6,376,461 | B1 | 4/2002 | Igari et al. |
| 6,419,961 | B1 | 7/2002 | Igari et al. |
| 6,613,358 | B2 | 2/2003 | Randolph et al. |
| 6,534,055 | B1 | 3/2003 | June et al. |
| 6,589,548 | B1 | 7/2003 | Oh et al. |
| 6,682,736 | B1 | 1/2004 | Hanson et al. |
| 6,692,964 | B1 | 2/2004 | June et al. |
| 6,699,500 | B2 | 3/2004 | Okada et al. |
| 6,740,634 | B1 | 5/2004 | Saikawa et al. |
| 6,887,466 | B2 | 5/2005 | June et al. |
| 6,905,681 | B1 | 6/2005 | June et al. |
| 6,984,720 | B1 | 1/2006 | Korman et al. |
| 7,488,802 | B2 | 2/2009 | Collins et al. |
| 7,498,171 | B2 | 3/2009 | Hariri et al. |
| 7,605,238 | B2 | 10/2009 | Korman et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 9,499,514 | B2 | 11/2016 | Hansen et al. |
| 2012/0122865 | A1 | 5/2012 | Muller et al. |
| 2012/0252844 | A1 | 10/2012 | Dewitt |
| 2014/0328832 | A1 | 11/2014 | Chopra et al. |

FOREIGN PATENT DOCUMENTS

| | | |
|---|---|---|
| WO | WO 2009/145899 A1 | 12/2009 |
| WO | WO 2010/036959 A2 | 4/2010 |
| WO | WO 2010/053732 A1 | 5/2010 |
| WO | WO 2010/089411 A2 | 8/2010 |
| WO | WO 2011/066342 A2 | 6/2011 |
| WO | WO 2011/082400 A2 | 7/2011 |
| WO | WO 2011/159877 A2 | 12/2011 |
| WO | WO 2011/161699 A2 | 12/2011 |
| WO | WO 2016/007848 A1 | 1/2016 |

OTHER PUBLICATIONS

Fourcade et al., "Upregulation of Tim-3 and PD-1 expression is associated with tumor antigen-specific CD8+ T cell dysfunction in melanoma patients," *J. Exp. Med.*, 207(10):2175-2186 (2010).

Gatley et al., "Deuterioglucose: alteration of biodistribution by an isotope effect," *J. Nucl. Med.*, 27(3):388-394 (1986).

Goodson, "Medical Applications of Controlled Release," vol. 2, CRC Press, Inc., Boca Raton, FL, pp. 115-138 (1984).

Gordon et al., "The metabolism of the abortifacient terpene, (R)-(+)-pulegone, to a proximate toxin, menthofuran," *Drug Metab. Dispos.*, 15(5):589-594 (1987).

Kushner et al., "Pharmacological uses and perspectives of heavy water and deuterated compounds," Can. J. Physiol. Pharmacol, 77(2):79-88 (1999).

Langer, "New methods of drug delivery," *Science*, 249:1527-1533 (1990).

Lijinsky et al., "Dose-response studies in carcinogenesis by nitroso-N-methyl-N-(2-phenyl)ethylamine in rats and the effects of deuterium substitution," *Food Chem. Toxicol.*, 20(4);393-399 (1982).

Lijinsky et al., "Dose-response studies with nitrosoheptamethyleneimine and its alpha-deuterium-labeled derivative in F344 rats," *J. Natl. Cancer Instit.*, 69(5):1127-1133 (1982).

Loo et al., "Development of an Fc-enhanced anti-B7-H3 monoclonal antibody with potent antitumor activity," *Clin. Cancer Res.*, 18(14):3834-3845 (2012).

Mangold et al., "Effects of deuterium labeling on azido amino acid mutagenicity in *Salmonella typhimurium*," *Mutat. Res.*, 308(1):33-42 (1994).

Oncology Tools, Dose Calculator and Dose Calculator Results, U.S. Food and Drug Administration, Center for Drug Evaluation and Research (2008), retrieved on the internet URL:https://web.archive.org/web/20080223150428/http://www.fda.gov/cder/cancer/animalframe.htm, retrieved on Jan. 24, 2017, 1 page.

Pardoll, "The blockade of immune checkpoints in cancer immunotherapy," *Nat. Rev. Cancer*, 12(4):252-264 (2012).

Penichet et al., "Antibody-cytokine fusion proteins for the therapy of cancer," *J. Immunol. Methods*, 284:91-101 (2001).

Roitt et al., Immunology, Third Edition, Mosby, St. Louis, MO, 17.1-17.12 (1993).

Sakuishi et al., "Targeting Tim-3 and PD-1 pathways to reverse T cell exhaustion and restore anti-tumor immunity," *J. Exp. Med.*, 207(10):2187-2194 (2010).

Saudek et al., "A preliminary trial of the programmable implantable medication system for insulin delivery," *N. Engl. J. Med.*, 321(9):574-579 (1989).

Sefton, "Implantable pumps," *Crit. Rev. Biomed. Eng.*, 14(3):201-240 (1987).

Stockdale, Medicine, vol. 3, Rubenstein and Federman, eds., Chapter 12, Section IV and Section X (1998).

Straathof et al., "An inducible caspase 9 safety switch for T-cell therapy," *Blood*, 105(11):4247-4254 (2005).

Taylor et al., "Protamine is an inhibitor of angiogenesis," *Nature*, 297:307-312 (1982).

Therasse et al., "New guidelines to evaluate the response to treatment in solid tumors. European Organization for Research and Treatment of Cancer, National Cancer Institute of the United States, National Cancer Institute of Canada," *J. Natl. Cancer Inst.*, 92(3):205-216 (2000).

Wade, "Deuterium isotope effects on noncovalent interactions between molecules," *Chem. Biol. Interact.*, 117:191-217 (1999).

Zello et al., "Plasma and urine enrichments following infusion of L-[1-13C]phenylalanine and L-[ring-2H5]phenylalanine in humans: evidence for an isotope effect in renal tubular reabsorption," *Metabolism*, 43(4):487-491 (1994).

ANTIPROLIFERATIVE COMPOUNDS, AND THEIR PHARMACEUTICAL COMPOSITIONS AND USES

1. CROSS REFERENCE TO RELATED APPLICATIONS

This application claims the benefit of the priority of U.S. Provisional Application No. 62/276,763, filed Jan. 8, 2016, the disclosure of which is incorporated herein by reference in its entirety.

2. FIELD

Provided herein are compounds of Formula A-I or B-I or a stereoisomer or mixture of stereoisomers, tautomer, pharmaceutically acceptable salt, solvate, hydrate, co-crystal, clathrate, isotopologue or polymorph thereof for treating, preventing or managing cancer. Also provided are pharmaceutical compositions comprising the compounds and methods of use of the compounds and compositions. In certain embodiments, the methods encompass treating, preventing or managing cancer, including solid tumors and blood borne tumors using the compounds provided herein In certain embodiments, the methods encompass treating, preventing or managing cancer, including acute myeloid leukemia and myelodysplastic syndrome, using the compounds provided herein.

3. BACKGROUND OF THE DISCLOSURE

3.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to, diabetic retinopathy, retinopathy of prematurity, corneal graft rejection, neovascular glaucoma, retrolental fibroplasia, arthritis, and proliferative vitreoretinopathy.

Accordingly, compounds that can control angiogenesis or inhibit the production of certain cytokines, including TNFα, may be useful in the treatment and prevention of various diseases and conditions.

3.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there is a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

4. SUMMARY

Provided herein are compounds, pharmaceutical compositions containing the compounds and methods of use thereof in treating cancer, including solid tumors and blood borne tumors. In one embodiment, the compounds for use in the compositions and methods provided herein are of Formula A-I or a stereoisomer or mixture of stereoisomers, tautomer, pharmaceutically acceptable salt, solvate, hydrate, co-crystal, clathrate, isotopologues or polymorph thereof (Compound A) or of Formula B-I or a stereoisomer or mixture of stereoisomers, tautomer, pharmaceutically salt, solvate, hydrate, co-crystal, clathrate, isotopologues or polymorph thereof (Compound B).

In certain embodiments, provided herein are compounds of Formula A-I:

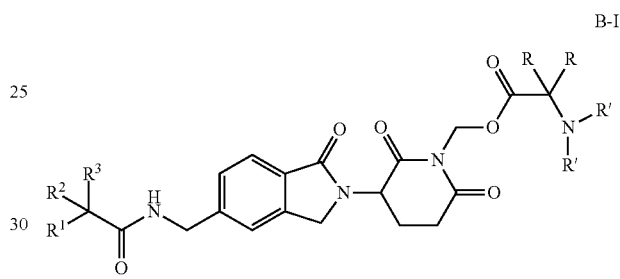

A-I or a stereoisomer or mixture of stereoisomers, tautomer, pharmaceutically acceptable salt, solvate, hydrate, co-crystal, clathrate, isotopologues or polymorph thereof (Compound A), wherein:

R is H, optionally substituted alkyl, or optionally substituted cycloalkyl;

$R^1$ is optionally substituted cycloalkyl, optionally substituted aryl, optionally substituted heteroaryl or optionally substituted heterocyclyl;

$R^2$ and $R^3$ are each halo; and where the substituents on $R^1$, when present, are one to three groups Q, where each Q is independently alkyl, halo, haloalkyl, hydroxyl, alkoxy, optionally substituted cycloalkyl; optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl or haloalkyl.

In other embodiments, provided herein are compounds of Formula B-I:

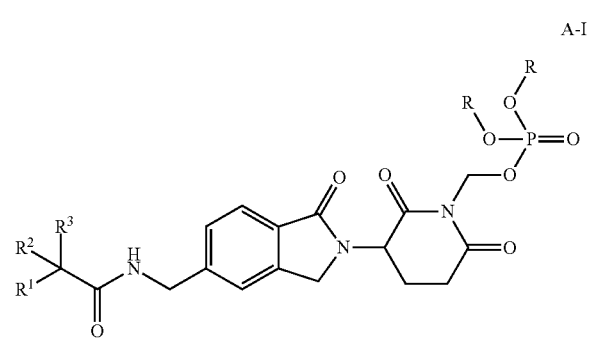

B-I or a stereoisomer or mixture of stereoisomers, tautomer, pharmaceutically acceptable salt, solvate, hydrate, co-crystal, clathrate, isotopologues or polymorph thereof (Compound B), wherein:

R is H, optionally substituted alkyl, or optionally substituted cycloalkyl;

R' is H or optionally substituted alkyl;

$R^1$ is optionally substituted cycloalkyl, optionally substituted aryl, optionally substituted heteroaryl or optionally substituted heterocyclyl;

$R^2$ and $R^3$ are each halo; and where the substituents on $R^1$, when present, are one to three groups Q, where each Q is independently alkyl, halo, haloalkyl, hydroxyl, alkoxy, optionally substituted cycloalkyl; optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl or haloalkyl.

In one aspect provided herein are pharmaceutical compositions containing Compound A or Compound B, and methods of use thereof in treating cancer, including solid tumors and blood borne tumors.

In one embodiment, the compound provided herein is a compound of formula A-I. In one embodiment, the compound provided herein is a tautomer of the compound of formula A-I. In one embodiment, the compound provided herein is a pharmaceutically acceptable salt of the compound of formula A-I. In one embodiment, the compound provided herein is a solvate of the compound of formula A-I. In one embodiment, the compound provided herein is a hydrate of compound of formula A-I. In one embodiment, the compound provided herein is a clathrate of the compound of formula A-I. In one embodiment, the compound provided herein is an isotopologue of the compound of formula A-I.

In one embodiment, the compound provided herein is a compound of formula B-I. In one embodiment, the compound provided herein is a tautomer of the compound of formula B-I. In one embodiment, the compound provided herein is a pharmaceutically acceptable salt of the compound of formula B-I. In one embodiment, the compound provided herein is a solvate of the compound of formula B-I. In one embodiment, the compound provided herein is a hydrate of compound of formula B-I. In one embodiment, the compound provided herein is a clathrate of the compound of formula B-I. In one embodiment, the compound provided herein is an isotopologue of the compound of formula B-I.

Also provided are pharmaceutical compositions formulated for administration by an appropriate route and means containing effective concentrations of one or more of the compounds provided herein and optionally comprising at least one pharmaceutical carrier.

In one embodiment, the pharmaceutical compositions deliver amounts effective for the treatment of cancer, including solid tumors and blood borne tumors. In one embodiment, the pharmaceutical compositions deliver amounts effective for the prevention of cancer, including solid tumors and blood borne tumors. In one embodiment, the pharmaceutical compositions deliver amounts effective for the amelioration of cancer, including solid tumors and blood borne tumors.

Also provided herein are combination therapies using one or more compounds or compositions provided herein, in combination with a therapy e.g., another pharmaceutical agent with activity against cancer or its symptoms. Examples of therapies within the scope of the methods include, but are not limited to, surgery, chemotherapy, radiation therapy, hormonal therapy, biological therapy, immunotherapy, and combinations thereof.

The compounds or compositions provided herein may be administered simultaneously with, prior to, or after administration of one or more of the above therapies. Pharmaceutical compositions containing Compound A or Compound B provided herein and one or more of the above agents are also provided.

In certain embodiments, provided herein are methods of treating, preventing or ameliorating cancer, including solid tumors and blood borne tumors, or one or more symptoms or causes thereof. In certain embodiments, provided herein are methods of treating cancer, including solid tumors and blood borne tumors, or one or more symptoms or causes thereof. In certain embodiments, provided herein are methods of preventing cancer, including solid tumors and blood borne tumors, or one or more symptoms or causes thereof. In certain embodiments, provided herein are methods of ameliorating cancer, including solid tumors and blood borne tumors, or one or more symptoms or causes thereof. In certain embodiments, the blood borne tumor is leukemia. In certain embodiments, methods provided herein encompass methods of treating various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of preventing various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of managing various forms of leukemias such as chronic lymphocytic leukemia, chronic myeloid leukemia, acute lymphocytic leukemia, acute myeloid leukemia and acute myeloblastic leukemia. The methods provided herein include treatment of leukemias that are relapsed, refractory or resistant. The methods provided herein include prevention of leukemias that are relapsed, refractory or resistant. The methods provided herein include management of leukemias that are relapsed, refractory or resistant. In one embodiment, methods provided herein encompass methods of treating acute myeloid leukemia. In one embodiment, methods provided herein encompass methods of preventing acute myeloid leukemia. In one embodiment, methods provided herein encompass methods of managing acute myeloid leukemia. In one embodiment, methods provided herein encompass methods of treating a myelodysplastic syndrome. In one embodiment, methods provided herein encompass methods of preventing a myelodysplastic syndrome. In one embodiment, methods provided herein encompass methods of managing a myelodysplastic syndrome. In one embodiment the compounds described herein may be used in a method of treating, preventing and/or ameliorating any of the diseases described herein.

In practicing the methods, effective amounts of the compounds or compositions containing therapeutically effective concentrations of the compounds are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. DETAILED DESCRIPTION

The compounds, methods and compositions are described in detail in the sections below.

5.1. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a radical having the formula —NR'R" wherein R' and R" are each independently hydrogen, alkyl or haloalkyl. An "optionally substituted amino" refers to a radical having the formula —NR'R" wherein one or both of R' and R" are optionally substituted alkyl as defined herein.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a stable monovalent monocyclic or bicyclic hydrocarbon group consisting solely of carbon and hydrogen atoms, having from three to ten carbon atoms which is saturated, e.g., cyclopropyl, cyclobutyl, cyclopentyl, cyclohexyl, decalinyl, norbornane, norbornene, adamantyl, bicyclo[2.2.2]octane and the like.

"Halo, "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethylethyl.

"Heterocycle" or "Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structure at any heteroatom or carbon atom which results in the creation of a stable compound. Exemplary heterocyclic radicals include, morpholinyl, piperidinyl, piperazinyl, pyranyl, pyrrolidinyl, oxetanyl, azetidinyl, quinuclidinyl, octahydroquinolizinyl, decahydroquinolizinyl, azabicyclo[3.2.1]octanyl, azabicyclo[2.2.2]octanyl, isoindolinyl, indolinyl and others.

"Heteroaryl" refers to a heterocyclyl group as defined above which is aromatic. The heteroaryl groups include, but are not limited to monocyclyl, bicyclyl and tricyclyl groups, and may be attached to the main structure at any heteroatom or carbon atom which results in the creation of a stable compound. Examples of such heteroaryl groups include, but are not limited to: furanyl, imidazolyl, oxazolyl, isoxazolyl, pyrimidinyl, pyridinyl, pyridazinyl, thiazolyl, thienyl, benzimidazolyl, imidazo[4,5-b]pyridinyl, imidazo[1,2-a]pyridinyl, imidazo[1,2-b]pyridazinyl, imidazo[1,2-a]pyrazinyl and others.

"$IC_{50}$" refers to an amount, concentration or dosage of a particular test compound that achieves a 50% inhibition of a maximal response, such as cell growth or proliferation, measured via any of the in vitro or cell based assay described herein.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

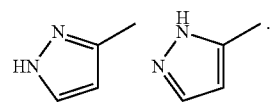

As readily understood by one skilled in the art, a wide variety of functional groups and other structures may exhibit tautomerism and all tautomers of Compound A or Compound B are within the scope of the present invention.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

Unless stated otherwise specifically described in the specification, it is understood that the substitution can occur on any atom of the alkyl, alkenyl, alkynyl, cycloalkyl, heterocyclyl, aryl or heteroaryl group.

Where the number of any given substituent is not specified (e.g., haloalkyl), there may be one or more substituents present. For example, "haloalkyl" may include one or more of the same or different halogens.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

In the description herein, if there is any discrepancy between a chemical name and chemical structure, the structure controls.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer, including solid tumors and blood borne tumors, are candidates for preventive regimens. Generally, the term "preventing" refers to administration of the drug prior to the onset of symptoms, particularly to patients at risk of cancer, including solid tumors and blood borne tumors.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" is an animal, typically a mammal, including a human, such as a human patient.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV 1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of leukemia after therapy have a return of leukemia cells in the marrow and a decrease in normal blood cells.

The term "refractory or resistant" refers to a circumstance where patients, even after intensive treatment, have residual leukemia cells in their marrow.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, a compound provided herein and another anti-cancer agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect from treatment with the compound of Formula I.

The term "biological therapy" refers to administration of biological therapeutics such as cord blood, stem cells, growth factors and the like.

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

"Anti-cancer agents" refer to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, checkpoint inhibitors and radiation treatment.

As used herein, overall survival (OS) means the time from randomization in a clinical trial until death from any cause. As used herein, progression-free survival (PFS) means the time from randomization in a clinical trial until progression or death. As used herein, event-free survival (EFS) means the time from study entry until any treatment failure, including disease progression, treatment discontinuation for any reason, or death. As used herein, overall response rate (ORR) means the sum of the percentage of patients who achieve complete and partial responses. As used herein, duration of response (DoR) is the time from achieving a response until relapse or disease progression.

Citation or identification of any reference in this application is not to be construed as an admission that the reference is prior art to the present application.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

5.2. Compounds

In certain embodiments, provided herein are compounds of Formula A-I:

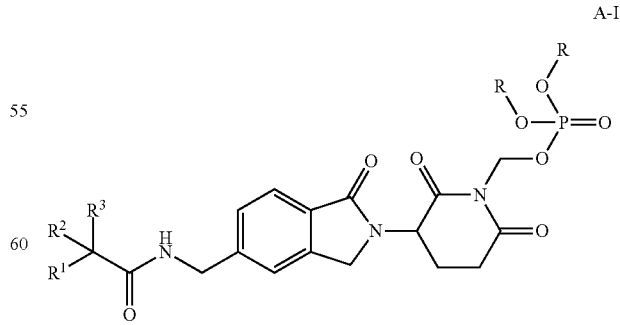

A-I or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

R$^1$ is optionally substituted cycloalkyl, optionally substituted aryl, optionally substituted heteroaryl or optionally substituted heterocyclyl;

R$^2$ and R$^3$ are each halo; and where the substituents on R$^1$, when present are one to three groups Q, where each Q is independently alkyl, halo, haloalkyl, hydroxyl, alkoxy, optionally substituted cycloalkyl; optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

J is O or S;

each R$^4$ is independently alkylene, alkenylene or a direct bond;

each R$^5$ is independently hydrogen, alkyl, haloalkyl or hydroxyalkyl; and

R$^6$ and R$^7$ are each independently hydrogen or alkyl, or R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, provided herein are compounds of Formula A-II:

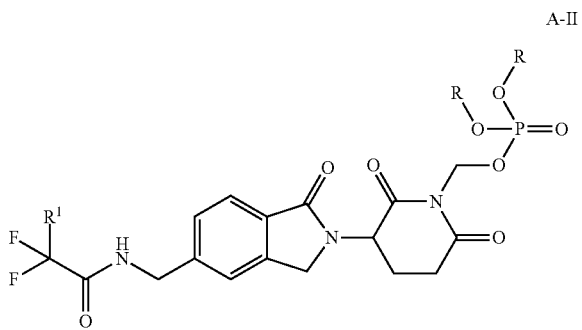

A-II or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

R$^1$ is optionally substituted cycloalkyl, optionally substituted aryl, optionally substituted heteroaryl or optionally substituted heterocyclyl;

where the substituents on R$^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

J is O or S;

each R$^4$ is independently alkylene, alkenylene or a direct bond;

each R$^5$ is independently hydrogen, alkyl, haloalkyl or hydroxyalkyl; and

R$^6$ and R$^7$ are each independently hydrogen or alkyl or R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula A-I or of Formula A-II, wherein R is H or (C$_1$-C$_6$)alkyl; R$^1$ is optionally substituted aryl, optionally substituted cycloalkyl, optionally substituted heterocyclyl, or optionally substituted heteroaryl, where the substituents on R$^1$, when present, are one to three groups Q, where each Q is independently halo, alkyl, optionally substituted cycloalkyl, optionally substituted aryl, —R$^4$OR$^5$, or —R$^4$N(R$^6$)(R$^7$); each R$^4$ is independently a direct bond or alkylene; each R$^5$ is independently hydrogen, halo, alkyl, alkoxy, haloalkoxy, or haloalkyl; and R$^6$ and R$^7$ are each independently hydrogen or alkyl, or R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula A-I or Formula A-II, wherein R is H or (C$_1$-C$_6$)alkyl; R$^1$ is optionally substituted phenyl, optionally substituted cyclohexyl, optionally substituted piperidinyl, or optionally substituted pyridyl, where the substituents on R$^1$, when present, are one to three groups Q, where each Q is independently halo, alkyl, —R$^4$OR$^5$ or —R$^4$N(R$^6$)(R$^7$); each R$^4$ is independently a direct bond or alkylene; each R$^5$ is independently hydrogen, halo, alkyl, alkoxy, haloalkoxy or haloalkyl; and R$^6$ and R$^7$ are each independently hydrogen or alkyl; or ii) R$^6$ and R$^7$ together with the nitrogen atom on which they are substituted form a 5 or 6-membered heterocyclyl ring.

In one embodiment, the compounds have Formula A-I or of Formula A-II, R is H or (C$_1$-C$_6$)alkyl; wherein R$^1$ is optionally substituted phenyl, optionally substituted cyclohexyl, optionally substituted piperidinyl, or optionally substituted pyridyl, where the substituents on R$^1$, when present are one to three groups Q, where each Q is independently bromo, fluoro, chloro, methyl, isopropyl, tert butyl trifluromethyl, methoxy, ethoxy, isopropyloxy, methoxyethoxy, isopropyloxyethoxy, trifluoromethoxy, methylamino, dimethylamino or piperidinyl.

In one embodiment, the compounds have Formula A-I or Formula A-II, wherein R is H or (C$_1$-C$_6$)alkyl; R$^1$ is optionally substituted aryl, where the substituents on R$^1$, when present, are one to three groups Q, where each Q is independently halo, alkyl, —R$^4$OR$^5$, —R$^4$SR$^5$ or R$^4$OR$^4$C(O)N(R$^6$)(R$^7$); each R$^4$ is independently a direct bond or alkylene; each R$^5$ is independently hydrogen, halo, alkyl or haloalkyl; and R$^6$ and R$^7$ are each independently hydrogen or alkyl.

In one embodiment, the compounds have Formula A-I or Formula A-II, wherein R is H or (C$_1$-C$_6$)alkyl; R$^1$ is optionally substituted aryl, where the substituents on R$^1$, when present, are one to three groups Q, where each Q is independently fluoro, chloro, methyl, —R$^4$OR$^5$, —R$^4$N(R$^6$)(R$^7$), —R$^4$SR$^5$ or R$^4$OR$^4$C(O)N(R$^6$)(R$^7$); each R$^4$ is independently a direct bond or methylene; each R⁵ is independently hydrogen, methyl, ethyl or trifluoromethyl; and R⁶ and R⁷ are each independently hydrogen or methyl.

In one embodiment, the compounds have Formula A-I or Formula A-II, wherein R is H or $(C_1-C_6)$alkyl; R¹ is optionally substituted phenyl, where the substituents on R¹, when present, are one to three groups Q, where each Q is independently fluoro, chloro, methyl, tert butyl, —R⁴OR⁵, —R⁴N(R⁶)(R⁷), —R⁴SR⁵ or R⁴OR⁴C(O)N(R⁶)(R⁷); each R⁴ is independently a direct bond or methylene; each R⁵ is independently hydrogen, methyl, ethyl or trifluoromethyl; and R⁶ and R⁷ are each independently hydrogen or methyl.

In one embodiment, provided herein are compounds of Formula A-III:

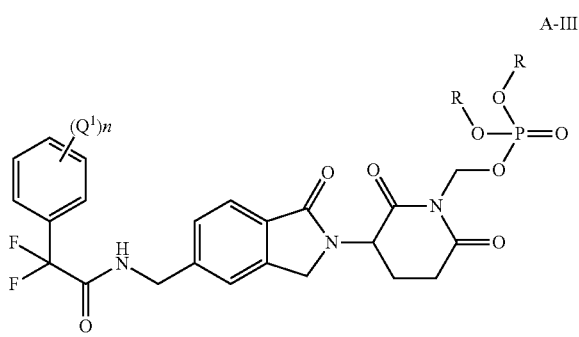

A-III or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

each Q¹ is independently alkyl, halo, haloalkyl, alkoxyalkyl, hydroxyl, alkoxy, optionally substituted cycloalkyl, optionally substituted cycloalkylalkyl, optionally substituted aryl —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl or hydroxyalkyl;

R⁶ and R⁷ are each independently hydrogen or alkyl or R⁶ and R⁷ together with the nitrogen atom on which they are substituted form a 5 or 6-membered heterocyclyl or heteroaryl ring, optionally substituted with one or two halo, alkyl or haloalkyl; and n is 0-3.

In one embodiment, provided herein are compounds of Formula A-III, wherein R is H or $(C^1-C^6)$alkyl and Q¹ is alkyl or halo. In another embodiment, provided herein are compounds of Formula A-III, wherein R is H and Q¹ is halo. In one embodiment, provided herein are compounds of Formula A-III, wherein R is H and Q¹ is fluoro or chloro.

In one embodiment, provided herein are compounds of Formula A-IV:

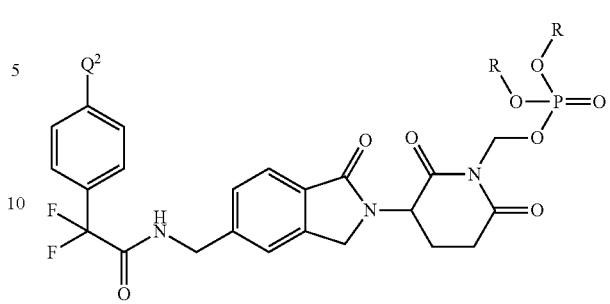

A-IV or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

Q² is hydrogen, alkyl, halo, haloalkyl, hydroxyl, alkoxy, optionally substituted cycloalkyl, optionally substituted cycloalkylalkyl, optionally substituted aryl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl or hydroxyalkyl; and

R⁶ and R⁷ are each independently hydrogen or alkyl.

In one embodiment, the compounds herein are of Formula A-IV, where R is H, optionally substituted alkyl, or optionally substituted cycloalkyl; Q² is hydrogen, halo, alkyl, optionally substituted aryl, —R⁴OR⁵ or —R⁴N(R⁶)(R⁷); R⁴ is independently a direct bond or alkylene; R⁵ is hydrogen, alkyl or haloalkyl; and R⁶ and R⁷ are each independently hydrogen or alkyl. In some embodiments, R is H, optionally substituted alkyl, or optionally substituted cycloalkyl; Q² is hydrogen, Br, Cl, F, methyl, isopropyl, t-butyl, isopropyl, —OCH₃, —C(CH₃)₂F, —OCH(CH₃)₂, —O(CH₂)₂OCH₃, or p-fluorophenyl.

In one embodiment, the compounds herein are of Formula A-IV, where R is independently H, optionally substituted alkyl, or optionally substituted cycloalkyl; and Q² is Br, Cl, or F.

In one embodiment, provided herein are compounds of Formula A-V:

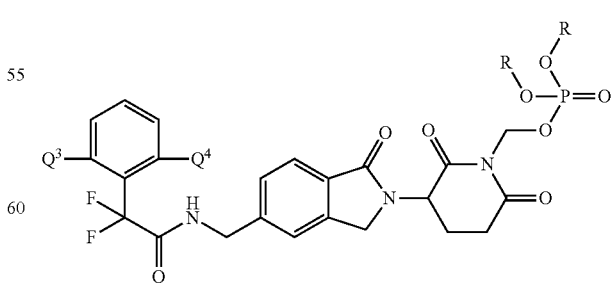

A-V or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

$Q^3$ and $Q^4$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, hydroxyalkyl, or alkoxyalkyl; and $R^6$ and $R^7$ are each independently hydrogen or alkyl.

In one embodiment, the compounds herein are of Formula A-V, where R is H, optionally substituted alkyl, or optionally substituted cycloalkyl; $Q^4$ and $Q^3$ are each independently hydrogen, halo, alkyl, alkoxyalkyl, —$R^4OR^5$, or —$R^4N(R^6)(R^7)$; $R^4$ is a direct bond or alkylene; and $R^5$ is hydrogen, alkyl or haloalkyl; and $R^6$ and $R^7$ are each independently hydrogen or alkyl. In some such embodiments, R is H, optionally substituted alkyl, or optionally substituted cycloalkyl; $Q^4$ and $Q^3$ are each independently hydrogen, F, methyl, —$CF_3$, OH, —$OCF_3$, —$OCH_2CH_3$, $OCH(CH_3)_2$, —$OCH_2CF_3$, or —$NHCH_3$.

In one embodiment, the compounds herein are of Formula A-V, R is H, optionally substituted alkyl, or optionally substituted cycloalkyl; where $Q^4$ is hydrogen; $Q^3$ is hydrogen, halo, alkyl, alkoxyalkyl, —$R^4N(R^6)(R^7)$, or —$R^4OR^5$; $R^4$ is a direct bond or alkylene; $R^5$ is hydrogen, alkyl or haloalkyl; and $R^6$ and $R^7$ are each independently hydrogen or alkyl.

In one embodiment, provided herein are compounds of Formula A-VI:

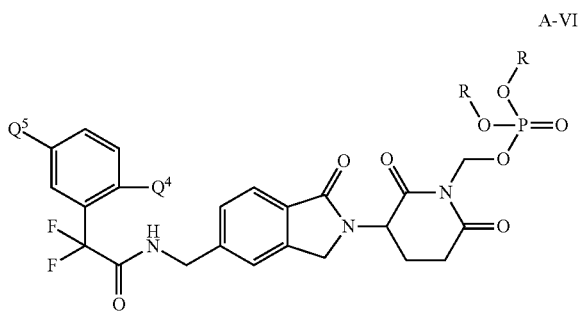

A-VI or a stereoisomer or mixture of stereoisomers, tautomer, pharmaceutically acceptable salt, solvate, hydrate, co-crystal, clathrate, or polymorph thereof, wherein: R is H, optionally substituted alkyl, or optionally substituted cycloalkyl;

$Q^4$ and $Q^5$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds herein are of Formula A-VI, where R is H, optionally substituted alkyl, or optionally substituted cycloalkyl; $Q^4$ and $Q^5$ are each independently hydrogen, halo, alkyl, alkoxyalkyl, —$R^4N(R^6)(R^7)$, or —$R^4OR^5$; $R^4$ is a direct bond or alkylene; $R^5$ is hydrogen, alkyl or haloalkyl; and $R^6$ and $R^7$ together with the nitrogen atom on which they are substituted form a 6-membered heterocyclyl. In some such embodiments, $Q^4$ and $Q^5$ are each independently hydrogen, F, Cl, OH, methyl, —$CF_3$, —$NHCH_3$, —$N(CH_3)_2$, —$OCF_3$, —$OCH_2CH_3$, —$OCH_2CF_3$, —$OCH(CH_3)_2$, —$O(CH_2)_2OCH_3$, —$O(CH_2)_2OCH(CH_3)_2$, —$O(CH_2)_2O(CH_2)_2OCH_3$, $O(CH_2)_2$-morpholinyl, piperidyl, morpholinyl, —$CH_2$-morpholinyl, or —$O(CH_2)_2$-4,4-difluoro-1-piperidyl.

In one embodiment, provided herein are compounds of Formula A-VII:

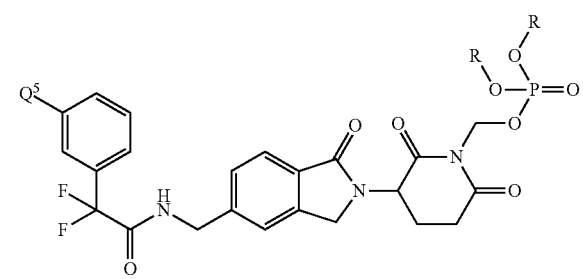

A-VII or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

$Q^5$ is hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds herein are of Formula A-VII, where R is H, optionally substituted alkyl, or optionally substituted cycloalkyl; $Q^5$ is hydrogen, halo, alkyl, alkoxyalkyl, —$R^4N(R^6)(R^7)$ or —$R^4OR^5$; $R^4$ is a direct bond or alkylene; and $R^5$ is hydrogen, alkyl or haloalkyl; and $R^6$ and $R^7$ together with the nitrogen atom on which they are substituted form a 6-membered heterocyclyl. In some such embodiments, $Q^5$ is hydrogen, F, Cl, methyl, piperidyl, morpholinyl, —$CH_2$-morpholinyl, —$N(CH_3)_2$, —$O(CH_2)_2OCH_3$, —$O(CH_2)_2OCH(CH_3)_2$, —$O(CH_2)_2O(CH_2)_2OCH_3$, or —$O(CH_2)_2$-4,4-difluoro-1-piperidyl.

In one embodiment, provided herein are compounds of Formula A-VIII:

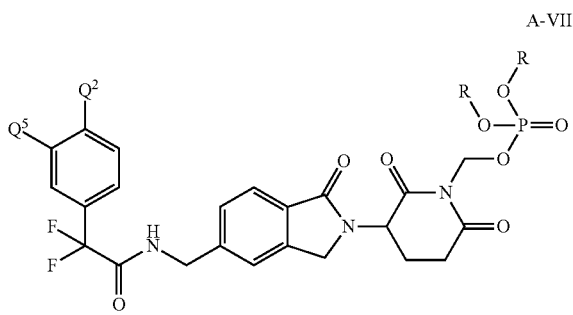

A-VIII or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

$Q^2$ and $Q^5$ are each independently hydrogen, alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl, or $R^6$ and $R^7$ together with the nitrogen atom on which they are substituted form a 6-membered heterocyclyl.

In one embodiment, the compounds herein are of Formula A-VIII, where R is H, optionally substituted alkyl, or optionally substituted cycloalkyl; $Q^2$ and $Q^5$ are each independently hydrogen, F, Br, Cl, methyl, isopropyl, t-butyl, —$C(CH_3)_2F$, p-fluorophenyl, cyclopropyl, —$N(CH_3)_2$, —$OCH_3$, —$OCH(CH_3)_2$, $O(CH_2)_2OCH_3$, —$O(CH_2)_2OCH(CH_3)_2$, —$O(CH_2)_2OCH_3$, —$O(CH_2)_2O(CH_2)_2OCH_3$, —$OCF_3$, —$O(CH_2)_2$-4,4-difluoro-1-piperidyl, —$SCF_3$, morpholinyl, piperidyl, or $CH_2$-morpholinyl.

In one embodiment, provided herein are compounds of Formula A-IX:

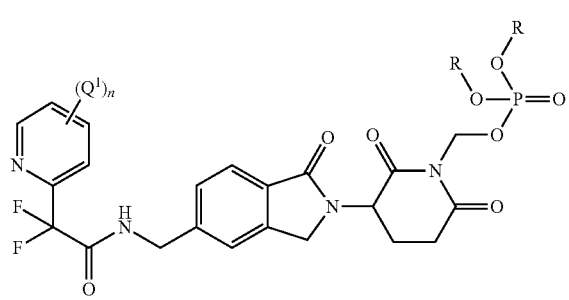

A-IX or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

each $Q^1$ is independently alkyl, halo, haloalkyl, alkoxyalkyl, hydroxyl, alkoxy, optionally substituted cycloalkyl; optionally substituted cycloalkylalkyl, optionally substituted heterocyclyl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;

J is O or S;

each $R^4$ is independently alkylene, alkenylene or a direct bond;

each $R^5$ is independently hydrogen, oxo, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, each independently selected from alkyl, haloalkyl or halo;

$R^6$ and $R^7$ are each independently hydrogen or alkyl;

$R^8$ is alkyl, haloalkyl, or hydroxyalkyl;

$R^9$ is alkyl or aryl;

J is O or S;

t is 1 or 2; and n is 0-3.

In one embodiment, the compounds herein are of Formula A-IX, where R is H, optionally substituted alkyl, or optionally substituted cycloalkyl; where each $Q^1$ is independently hydrogen, halo, alkyl, haloalkyl, alkoxyalkyl or haloalkoxyalkyl. In some embodiments, each $Q^1$ is independently fluoro, chloro, bromo, methyl, isopropyl, t-butyl, —$CF_3$, —O—$CH_2CH_3$, —O—$CH(CH_3)_2$, or cyclopropyl.

In one embodiment, the compound provided herein is selected from the group consisting of:

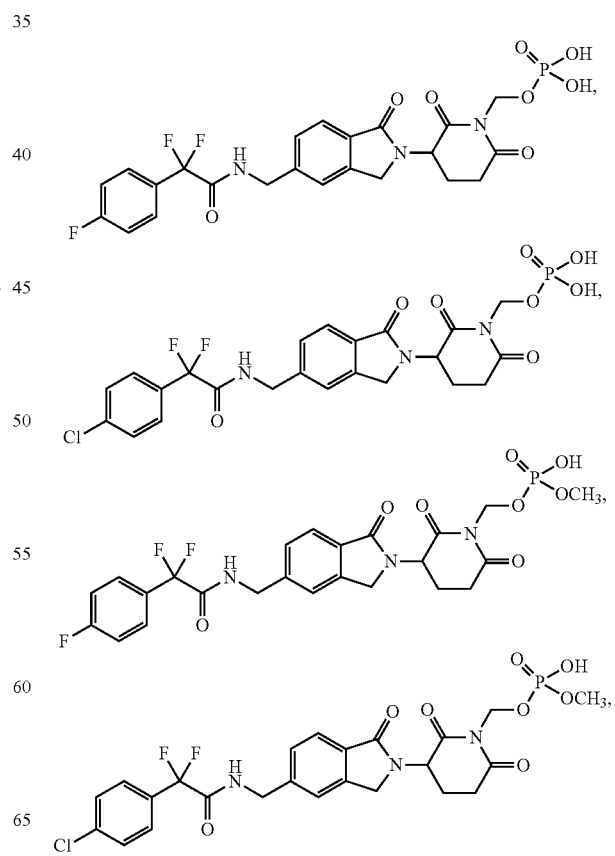

-continued

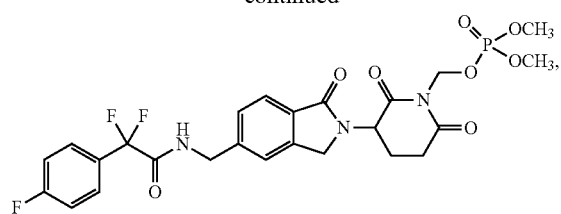
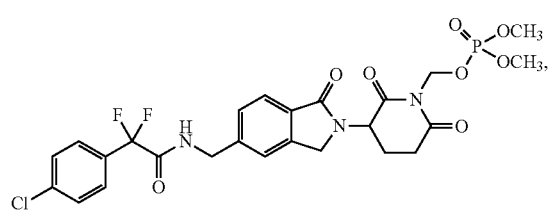
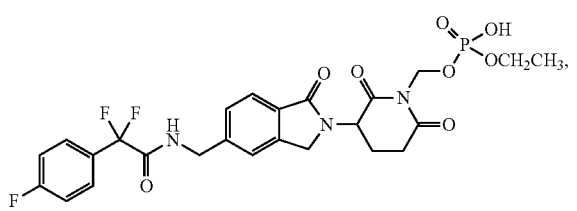
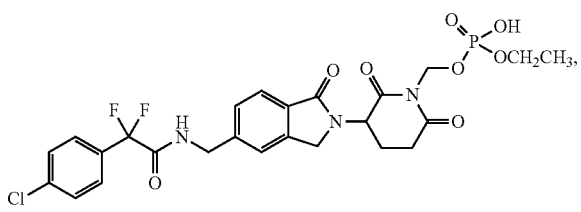
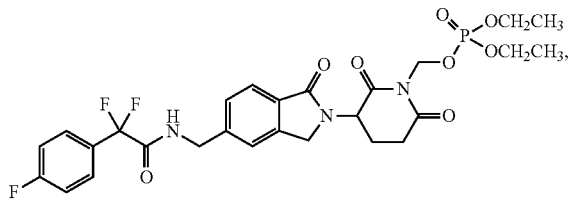
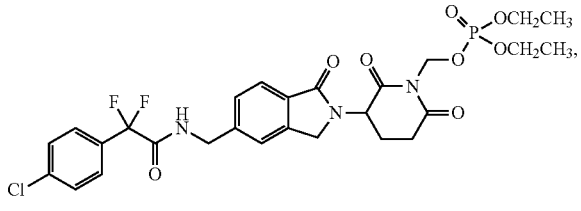
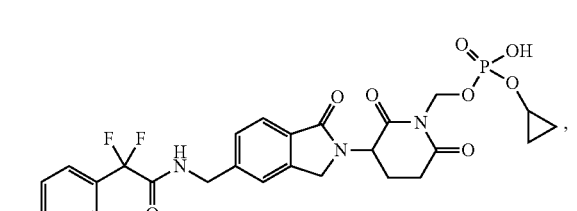
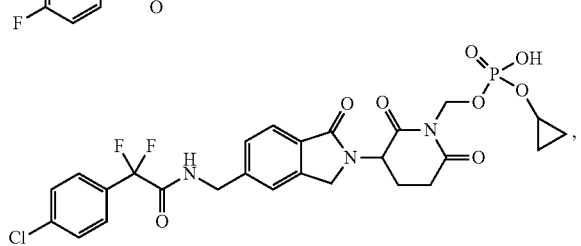

-continued

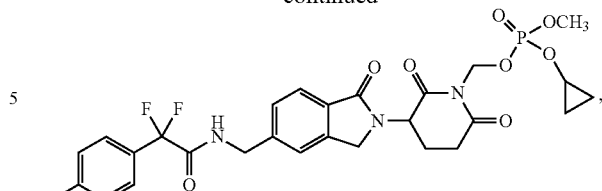
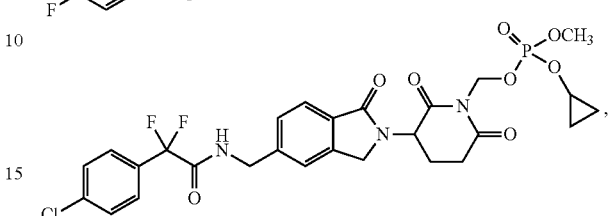
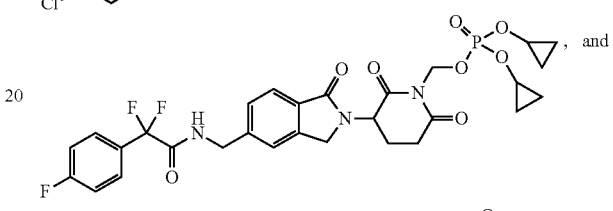
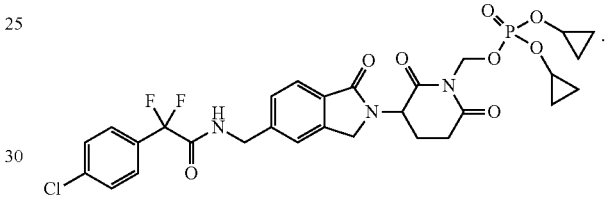

In one embodiment, the compound provided herein is a tautomer of the compound of formula A-I, A-II, A-III, A-IV, A-V, A-VI, A-VII, A-VIII, or A-IX. In one embodiment, the compound provided herein is a pharmaceutically acceptable salt of the compound of formula A-I, A-II, A-III, A-IV, A-V, A-VI, A-VII, A-VIII, or A-IX. In some such embodiments, the salt is a sodium, potassium, magnesium or calcium salt. In one embodiment, the compound provided herein is a solvate of the compound of formula A-I, A-II, A-III, A-IV, A-V, A-VI, A-VII, A-VIII, or A-IX. In one embodiment, the compound provided herein is a hydrate of compound of formula A-I, A-II, A-III, A-IV, A-V, A-VI, A-VII, A-VIII, or A-IX. In one embodiment, the compound provided herein is a clathrate of the compound of formula A-I, A-II, A-III, A-IV, A-V, A-VI, A-VII, A-VIII, or A-IX. In one embodiment, the compound provided herein is an isotopologue of the compound of formula A-I, A-II, A-III, A-IV, A-V, A-VI, A-VII, A-VIII, or A-IX.

In other embodiments, provided herein are compounds of Formula B-I:

B-I

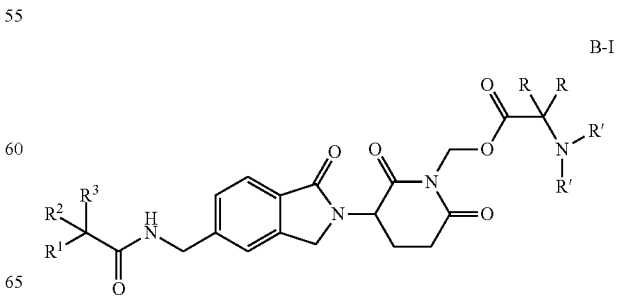

or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

R' is H or optionally substituted alkyl;

$R^1$ is optionally substituted cycloalkyl, optionally substituted aryl, optionally substituted heteroaryl or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, provided herein are compounds of Formula B-II:

B-II or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

R' is H or optionally substituted alkyl;

$R^1$ is optionally substituted cycloalkyl, optionally substituted aryl, optionally substituted heteroaryl or optionally substituted heterocyclyl;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula B-I or of Formula B-II, wherein

R is H or $(C_1$-$C_6)$alkyl;

R' is H or $(C_1$-$C_6)$alkyl;

$R^1$ is optionally substituted alkyl or optionally substituted aryl, where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula B-I or of Formula B-II, wherein R is H or $(C_1$-$C_6)$alkyl; R' is H or $(C_1$-$C_6)$alkyl; $R^1$ is optionally substituted aryl, optionally substituted cycloalkyl, optionally substituted heterocyclyl, or optionally substituted heteroaryl, where the substituents on $R^1$, when present are one to three groups Q, where each Q is independently halo, alkyl, optionally substituted cycloalkyl, optionally substituted aryl, —$R^4OR^5$, or $R^4N(R^6)(R^7)$; each $R^4$ is independently a direct bond or alkylene; each $R^5$ is independently hydrogen, halo, alkyl, alkoxy, haloalkoxy, or haloalkyl; and $R^6$ and $R^7$ are each independently hydrogen or alkyl, or $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula B-I or Formula B-II, wherein R is H or $(C_1$-$C_6)$alkyl; R' is H or $(C_1$-$C_6)$alkyl; $R^1$ is optionally substituted phenyl, optionally substituted cyclohexyl, optionally substituted piperidinyl, or optionally substituted pyridyl, where the substituents on $R^1$, when present, are one to three groups Q, where each Q is independently halo, alkyl, —$R^4OR^5$ or —$R^4N(R^6)(R^7)$; each $R^4$ is independently a direct bond or alkylene; each $R^5$ is independently hydrogen, halo, alkyl, alkoxy, haloalkoxy or haloalkyl; and $R^6$ and $R^7$ are each independently hydrogen or alkyl; or ii) $R^6$ and $R^7$ together with the nitrogen atom on which they are substituted form a 5 or 6-membered heterocyclyl ring.

In one embodiment, the compounds have Formula B-I or of Formula B-II, wherein R is H or $(C_1$-$C_6)$alkyl; R' is H or $(C_1$-$C_6)$alkyl; $R^1$ is optionally substituted phenyl, optionally substituted cyclohexyl, optionally substituted piperidinyl, or optionally substituted pyridyl, where the substituents on $R^1$, when present are one to three groups Q, where each Q is independently bromo, fluoro, chloro, methyl, isopropyl, tert butyl, trifluromethyl, methoxy, ethoxy, isopropyloxy, methoxyethoxy, isopropyloxyethoxy, trifluoromethoxy, methylamino, dimethylamino or piperidinyl.

In one embodiment, the compounds have Formula B-I or Formula B-II, wherein R is H or $(C_1$-$C_6)$alkyl; R' is H or $(C_1$-$C_6)$alkyl; $R^1$ is optionally substituted aryl, where the substituents on $R^1$, when present, are one to three groups Q, where each Q is independently halo, alkyl, —$R^4OR^5$, —$R^4SR^5$ or $R^4OR^4C(O)N(R^6)(R^7)$; each $R^4$ is independently a direct bond or alkylene; each $R^5$ is independently hydrogen, halo, alkyl or haloalkyl; and $R^6$ and $R^7$ are each independently hydrogen or alkyl.

In one embodiment, the compounds have Formula B-I or Formula B-II, wherein R is H or $(C_1-C_6)$alkyl; R' is H or $(C_1-C_6)$alkyl; $R^1$ is optionally substituted aryl, where the substituents on $R^1$, when present, are one to three groups Q, where each Q is independently fluoro, chloro, methyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

In one embodiment, the compounds have Formula B-I or Formula B-II, wherein R is H or $(C_1-C_6)$alkyl; R' is H or $(C_1-C_6)$alkyl; $R^1$ is optionally substituted phenyl, where the substituents on $R^1$, when present, are one to three groups Q, where each Q is independently fluoro, chloro, methyl, tert butyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

In one embodiment, provided herein are compounds of Formula B-III:

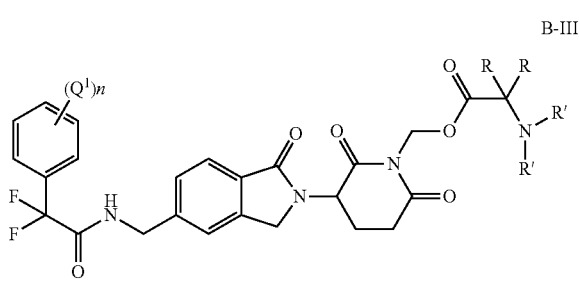

B-III or a stereoisomer or mixture of stereoisomers, tautomer, pharmaceutically acceptable salt, solvate, hydrate, co-crystal, clathrate, isotopologue or polymorph thereof, wherein:

R is H, optionally substituted alkyl, or optionally substituted cycloalkyl;

R' is H or optionally substituted alkyl;

each $Q^1$ is independently alkyl, halo, haloalkyl, alkoxyalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl;

$R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl; and n is 0-3.

In one embodiment, provided herein are compounds of Formula B-III, wherein R is H or $(C_1-C_6)$alkyl; R' is H; and $Q^1$ is alkyl or halo. In another embodiment, provided herein are compounds of Formula B-III, wherein one of the R is H and the other is an optionally substituted alkyl; R' is H; and $Q^1$ is halo. In one embodiment, provided herein are compounds of Formula B-III, wherein one of the R is H and the other is an optionally substituted alkyl; R' is H; and $Q^1$ is fluoro.

In one embodiment, provided herein are compounds of Formula B-IV:

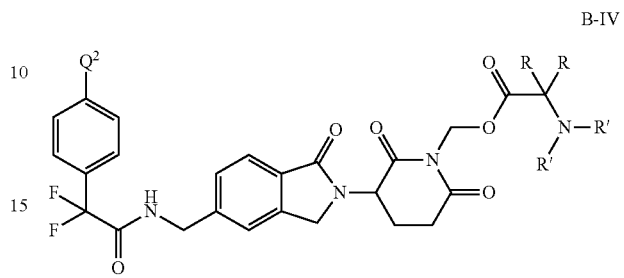

B-IV or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

$Q^2$ is hydrogen, alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl.

In one embodiment, the compounds herein are of Formula B-IV, where R is H, optionally substituted alkyl, or optionally substituted cycloalkyl; R' is H or optionally substituted alkyl; $Q^2$ is hydrogen, halo, alkyl, optionally substituted aryl, —$R^4OR^5$ or —$R^4N(R^6)(R^7)$; $R^4$ is independently a direct bond or alkylene; $R^5$ is hydrogen, alkyl or haloalkyl; and $R^6$ and $R^7$ are each independently hydrogen or alkyl. In some embodiments, R is H, optionally substituted alkyl, or optionally substituted cycloalkyl; R' is H or optionally substituted alkyl; $Q^2$ is hydrogen, Br, Cl, F, methyl, isopropyl, t-butyl, isopropyl, —$OCH_3$, —$SCH_3$, —$C(CH_3)_2F$, —$OCH(CH_3)_2$, —$O(CH_2)_2OCH_3$, or p-fluorophenyl.

In one embodiment, the compounds herein are of Formula B-IV, wherein R is independently H or optionally substituted alkyl; R' is independently H or optionally substituted alkyl; and $Q^2$ is Br, Cl, or F.

In one embodiment, provided herein are compounds of Formula B-V:

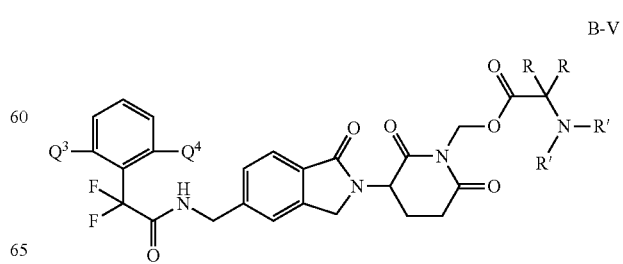

B-V or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

$Q^3$ and $Q^4$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, hydroxyalkyl, or alkoxyalkyl; and $R^6$ and $R^7$ are each independently hydrogen or alkyl.

In one embodiment, the compounds herein are of Formula B-V, where R is H, optionally substituted alkyl, or optionally substituted cycloalkyl; R' is H or optionally substituted alkyl; $Q^4$ and $Q^3$ are each independently hydrogen, halo, alkyl, alkoxyalkyl, —$R^4OR^5$, or —$R^4N(R^6)(R^7)$; $R^4$ is a direct bond or alkylene; and $R^5$ is hydrogen, alkyl or haloalkyl; and $R^6$ and $R^7$ are each independently hydrogen or alkyl. In some such embodiments, R is H, optionally substituted alkyl, or optionally substituted cycloalkyl; R' is H or optionally substituted alkyl; $Q^4$ and $Q^3$ are each independently hydrogen, F, methyl, $CF_3$, OH, —$OCF_3$, —$OCH_2CH_3$, $OCH(CH_3)_2$, —$OCH_2CF_3$, or —$NHCH_3$.

In one embodiment, the compounds herein are of Formula B-V, where R is H, optionally substituted alkyl, or optionally substituted cycloalkyl; R' is H or optionally substituted alkyl; $Q^4$ is hydrogen, $Q^3$ is hydrogen, halo, alkyl, alkoxyalkyl, —$R^4N(R^6)(R^7)$, or —$R^4OR^5$; $R^4$ is a direct bond or alkylene; $R^5$ is hydrogen, alkyl or haloalkyl; and $R^6$ and $R^7$ are each independently hydrogen or alkyl.

In one embodiment, provided herein are compounds of Formula B-VI:

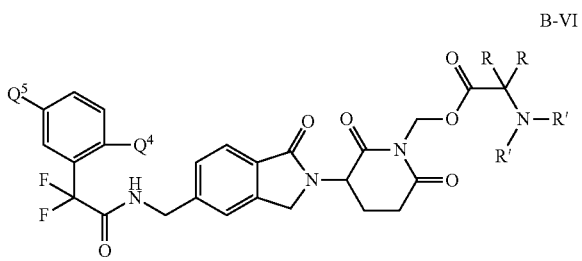

B-VI or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

$Q^4$ and $Q^5$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds herein are of Formula B-VI, where R is H, optionally substituted alkyl, or optionally substituted cycloalkyl; R' is H or optionally substituted alkyl; $Q^4$ and $Q^5$ are each independently hydrogen, halo, alkyl, alkoxyalkyl, —$R^4N(R^6)(R^7)$, or —$R^4OR^5$; $R^4$ is a direct bond or alkylene; $R^5$ is hydrogen, alkyl or haloalkyl; and $R^6$ and $R^7$ together with the nitrogen atom on which they are substituted form a 6-membered heterocyclyl. In some such embodiments, $Q^4$ and $Q^5$ are each independently hydrogen, F, Cl, OH, methyl, —$CF_3$, —$NHCH_3$, —$N(CH_3)_2$, —$OCF_3$, —$OCH_2CH_3$, —$OCH_2CF_3$, —$OCH(CH_3)_2$, —$O(CH_2)_2OCH_3$, —$O(CH_2)_2OCH(CH_3)_2$, —$O(CH_2)_2O(CH_2)_2OCH_3$, $O(CH_2)_2$-morpholinyl, piperidyl, morpholinyl, —$CH_2$-morpholinyl, or —$O(CH_2)_2$-4,4-difluoro-1-piperidyl.

In one embodiment, provided herein are compounds of Formula B-VII:

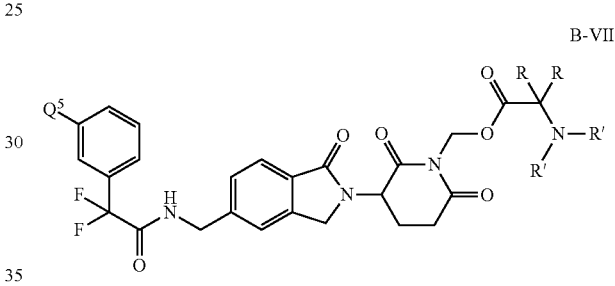

B-VII or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

$Q^5$ is hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compounds herein are of Formula B-VII, where R is H, optionally substituted alkyl, or optionally substituted cycloalkyl; R' is H or optionally substituted alkyl; $Q^5$ is hydrogen, halo, alkyl, alkoxyalkyl, —$R^4N(R^6)(R^7)$ or —$R^4OR^5$; $R^4$ is a direct bond or alkylene; and $R^5$ is hydrogen, alkyl or haloalkyl; and $R^6$ and $R^7$ together with the nitrogen atom on which they are substituted form a 6-membered heterocyclyl. In some such embodiments, R is H, optionally substituted alkyl, or optionally substituted cycloalkyl; $Q^5$ is hydrogen, F, Cl, methyl, piperidyl, morpholinyl, —CH$_2$-morpholinyl, —N(CH$_3$)$_2$, —O(CH$_2$)$_2$OCH$_3$, —O(CH$_2$)$_2$OCH(CH$_3$)$_2$, —O(CH$_2$)$_2$O(CH$_2$)$_2$OCH$_3$, or —O(CH$_2$)$_2$-4,4-difluoro-1-piperidyl.

In one embodiment, provided herein are compounds of Formula B-VIII:

B-VIII or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

Q$^2$ and Q$^5$ are each independently hydrogen, alkyl, halo, haloalkyl, hydroxyl, alkoxy, optionally substituted cycloalkyl, optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

J is O or S;

each R$^4$ is independently alkylene, alkenylene or a direct bond;

each R$^5$ is independently hydrogen, alkyl, haloalkyl or hydroxyalkyl; and

R$^6$ and R$^7$ are each independently hydrogen or alkyl, or R$^6$ and R$^7$ together with the nitrogen atom on which they are substituted form a 6-membered heterocyclyl.

In one embodiment, the compounds herein are of Formula B-VIII, where R is H, optionally substituted alkyl, or optionally substituted cycloalkyl; R' is H or optionally substituted alkyl; Q$^2$ and Q$^5$ are each independently hydrogen, halo, alkyl, alkoxyalkyl, optionally substituted aryl, or —R$^4$OR$^5$; R$^4$ is a direct bond or alkylene; and R$^5$ is hydrogen, alkyl or haloalkyl. In some such embodiments, R is H, optionally substituted alkyl, or optionally substituted cycloalkyl; Q$^2$ and Q$^5$ are each independently hydrogen, F, Br, Cl, methyl, isopropyl, t-butyl, —C(CH$_3$)$_2$F, p-fluorophenyl, cyclopropyl, —N(CH$_3$)$_2$, —OCH$_3$, —OCH(CH$_3$)$_2$, O(CH$_2$)$_2$OCH$_3$, —O(CH$_2$)$_2$OCH(CH$_3$)$_2$, —O(CH$_2$)$_2$OCH$_3$, —O(CH$_2$)$_2$O(CH$_2$)$_2$OCH$_3$, —O(CH$_2$)$_2$-4,4-difluoro-1-piperidyl, —SCF$_3$, morpholinyl, piperidyl, or CH$_2$-morpholinyl.

In one embodiment, provided herein are compounds of Formula B-IX:

B-IX or a stereoisomer or mixture of stereoisomers, tautomer, pharmaceutically acceptable salt, solvate, hydrate, co-crystal, clathrate, or polymorph thereof, wherein:

R is H, optionally substituted alkyl, or optionally substituted cycloalkyl;

R' is H or optionally substituted alkyl;

each Q$^1$ is independently alkyl, halo, haloalkyl, alkoxyalkyl, hydroxyl, alkoxy, optionally substituted cycloalkyl, optionally substituted cycloalkylalkyl, optionally substituted heterocyclyl, —R$^4$OR$^5$, —R$^4$OR$^5$—R$^4$OR$^5$, —R$^4$N(R$^6$)(R$^7$), —R$^4$SR$^5$, —R$^4$OR$^4$N(R$^6$)(R$^7$), —R$^4$OR$^4$C(J)N(R$^6$)(R$^7$), —C(J)R$^9$ or R$^4$S(O)$_t$R$^8$;

J is O or S;

each R$^4$ is independently alkylene, alkenylene or a direct bond;

each R$^5$ is independently hydrogen, oxo, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in R$^5$ are each independently optionally substituted with 1-3 Q$^1$ groups selected from alkyl, haloalkyl or halo;

R$^6$ and R$^7$ are each independently hydrogen or alkyl;

R$^8$ is alkyl, haloalkyl, or hydroxyalkyl;

R$^9$ is alkyl or aryl;

J is O or S;

t is 1 or 2; and n is 0-3.

In one embodiment, the compounds herein are of Formula B-IX, R is H, optionally substituted alkyl, or optionally substituted cycloalkyl; R' is H or optionally substituted alkyl; where each Q$^1$ is independently hydrogen, halo, alkyl, haloalkyl, alkoxyalkyl or haloalkoxyalkyl. In some embodiments, R is H, optionally substituted alkyl, or optionally substituted cycloalkyl; R' is H or optionally substituted alkyl, each is independently fluoro, chloro, bromo, methyl, isopropyl, t-butyl, —CF$_3$, —O—CH$_2$CH$_3$, —O—CH(CH$_3$)$_2$, or cyclopropyl.

In one embodiment, the compound provided herein is selected from the group consisting of:

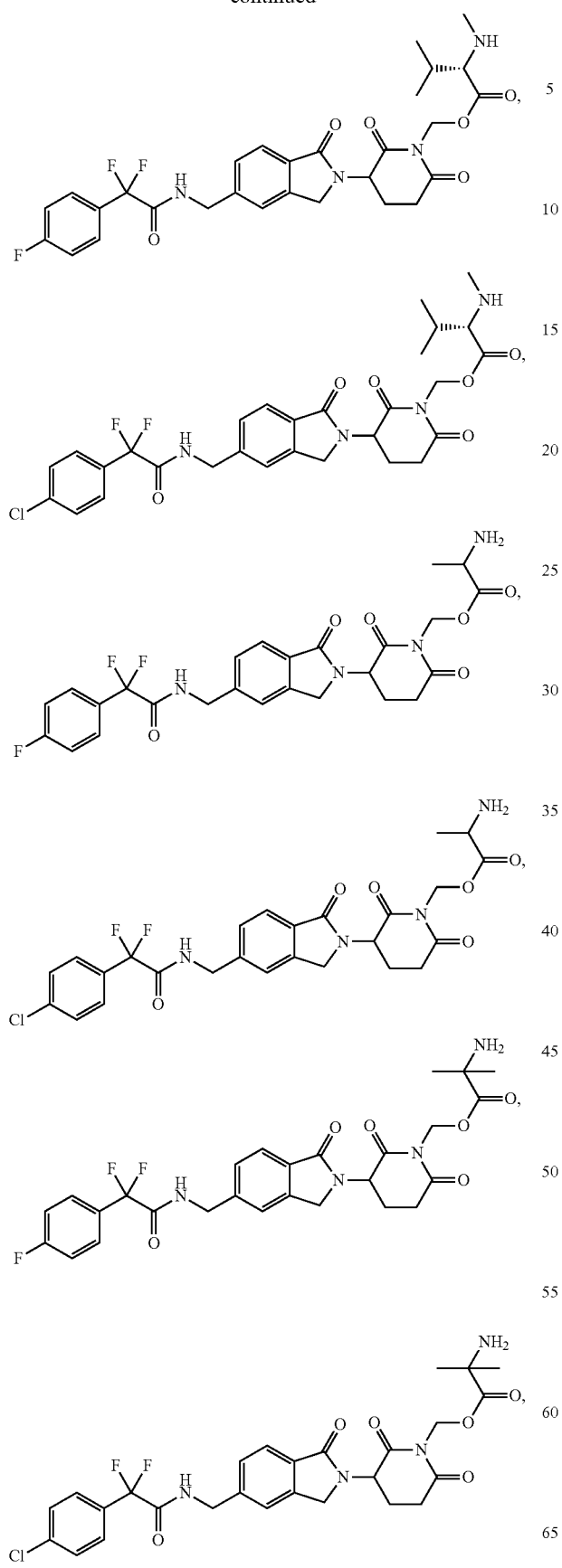

-continued

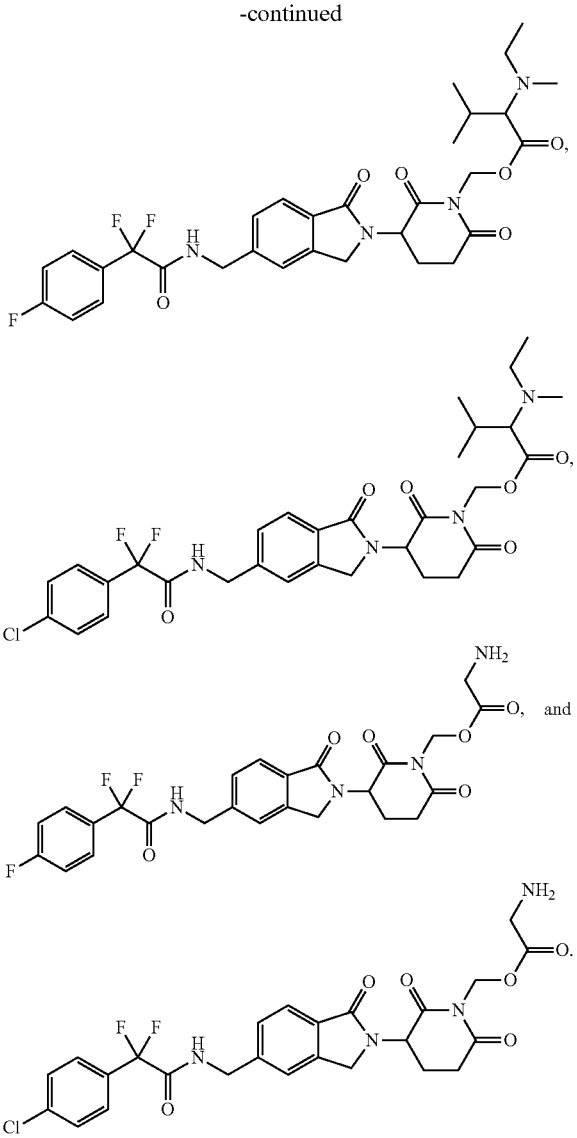

In one embodiment, the compound provided herein is a tautomer of the compound of formula B-I, B-II, B-IV, B-V, B-VI, B-VII, B-VIII, B-IX or B-X. In one embodiment, the compound provided herein is a pharmaceutically acceptable salt of the compound of formula B-I, B-II, B-III, B-IV, B-V, B-VI, B-VII, B-VIII, B-IX or B-X. In some such embodiments, the salt is a hydrochloric salt. In one embodiment, the compound provided herein is a solvate of the compound of formula B-I, B-II, B-III, B-IV, B-V, B-VI, B-VII, B-VIII, B-IX or B-X. In one embodiment, the compound provided herein is a hydrate of compound of formula B-I, B-II, B-III, B-IV, B-V, B-VI, B-VII, B-VIII, B-IX or B-X. In one embodiment, the compound provided herein is a clathrate of the compound of formula B-I, B-II, B-III, B-IV, B-V, B-VI, B-VII, B-VIII, B-IX or B-X. In one embodiment, the compound provided herein is an isotopologue of the compound of formula B-I, B-II, B-III, B-IV, B-V, B-VI, B-VII, B-VIII, B-IX or B-X.

Isotopologues of Compounds

Also provided herein are isotopically enriched analogs of the compounds ("isotopologues") provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

5.3. Methods of Treatment

In one embodiment, provided herein is a method of treating, preventing and managing cancer, which comprises administering to a patient Compound A or Compound B provided herein.

In one embodiment provided herein is a method of treating cancer, which comprises administering to a patient Compound A pr Compound B provided herein.

In one embodiment provided herein is a method of preventing cancer, which comprises administering to a patient Compound A or Compound B provided herein.

In another embodiment, provided herein is method of managing cancer, which comprises administering to a patient Compound A or Compound B provided herein.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4 colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of Compound A or Compound B provided herein.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7).

In certain embodiments, the methods of treating, preventing or managing acute myeloid leukemia in a subject comprise the step of administering to the subject an amount of Compound A or Compound B provided herein effective to treat, prevent or manage acute myeloid leukemia alone or in combination.

In one embodiment, provided herein are methods of treating, preventing or managing acute myeloid leukemia by intravenous administration of Compound A or Compound B.

In some embodiments, the methods comprise the step of administering to the subject Compound A or Compound B provided herein, in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of Compound A or Compound B provided herein, effective to treat, prevent or manage acute lymphocytic leukemia alone or in combination with a second active agent. In some embodiments, the methods comprise the step of administering to the subject Compound A or Compound B provided herein in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of Compound A or Compound B provided herein, effective to treat, prevent or manage chronic myelogenous leukemia. In some embodiments, the methods comprise the step of administering to the subject Compound A or Compound B provided herein, in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of Compound A or Compound B provided herein, effective to treat, prevent or manage chronic lymphocytic leukemia. In some embodiments, the methods comprise the step of administering to the subject Compound A or Compound B provided herein, in combination with a second active agent in amounts effective to treat, prevent or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In one embodiment, provided herein are methods of treating, preventing, and/or managing a myelodysplastic syndrome (MDS) by administering a therapeutically active amount of Compound A or Compound B provided herein. In one embodiment, the MDS is relapsed, resistant or refractory MDS. In one embodiment, MDS is selected from refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of Compound A or Compound B provided herein to a patient having relapsed/refractory multiple myeloma with impaired renal function.

In some embodiments, provided herein are Compounds A and Compounds B for use in a method of treating, preventing and/or managing any of the above-mentioned diseases or conditions.

In certain embodiments, a therapeutically or prophylactically effective amount of Compound A or Compound B provided herein is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day. In some such embodiments, the therapeutically or prophylactically effective amount is about 2, about 3, about 4, about 5, about 6 or about 7 mg per day.

In one embodiment, the recommended daily dose range of Compound A or Compound B provided herein, for the conditions described herein lie within the range of from about 0.05 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.1, 0.5, 1, 2, 3, 4, 5, 10, 15, 20, 25 or 50 mg per day. In another embodiment, the recommended starting dosage may be 0.1, 0.5, 1, 2, 3, 4, or 5 mg per day. The dose may be escalated to 15, 20, 25, 30, 35, 40, 45 and 50 mg/day. In a specific embodiment, Compound A or Compound B provided herein can be administered in an amount of about 25 mg/day to patients with leukemia, including AML. In a particular embodiment, Compound A or Compound B provided herein can be administered in an amount of about 10 mg/day to patients with leukemia, including AML. In a particular embodiment, Compound A or Compound B provided herein can be administered in an amount of about 5 mg/day to patients with leukemia, including AML. In a particular embodiment, Compound A or Compound B provided herein can be administered in an amount of about 4 mg/day to patients with leukemia, including AML. In a particular embodiment, Compound A or Compound B provided herein can be administered in an amount of about 3 mg/day to patients with leukemia, including AML.

In a specific embodiment, Compound A or Compound B can be administered in an amount of about 25 mg/day to patients with MDS. In a particular embodiment, Compound A or Compound B can be administered in an amount of about 10 mg/day to patients with MDS. In a particular embodiment, Compound A or Compound B can be administered in an amount of about 5 mg/day to patients with MDS. In a particular embodiment, Compound A or Compound B can be administered in an amount of about 4 mg/day to patients with MDS. In a particular embodiment, Compound A or Compound B provided herein can be administered in an amount of about 3 mg/day to patients with MDS. In a particular embodiment, Compound A or Compound B provided herein can be administered in an amount of about 2 mg/day to patients with MDS. In a particular embodiment, Compound A or Compound B provided herein can be administered in an amount of about 1 mg/day to patients with MDS. In a particular embodiment, Compound A or Compound B provided herein can be administered in an amount of about 0.5 mg/day to patients with MDS.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the amount of Compound A or Compound B provided herein administered is sufficient to provide a plasma concentration of Compound A or Compound B at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of Compound A or Compound B provided herein administered is sufficient to provide a plasma concentration of Compound A or Compound B at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of Compound A or Compound B provided herein. Once steady state is reached, there are minor peaks and troughs on the time dependent curve of the plasma concentration of the compound.

In certain embodiments, the amount of Compound A or Compound B provided herein administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of Compound A or Compound B provided herein administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, about 0.01 to about 20 µM, about 0.02 to about 20 µM, from about 0.02 to about 20 µM, or from about 0.01 to about 20 µM.

In certain embodiments, the amount of Compound A or Compound B provided herein administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of Compound A or Compound B provided herein. In certain embodiments, the patient to be treated with one of the methods provided herein has been treated with anticancer therapy prior to the administration of Compound A or Compound B provided herein. In certain embodiments, the patient to be treated with one of the methods provided herein has developed drug resistance to the anticancer therapy.

The methods provided herein encompass treating a patient regardless of patient's age, although some diseases or disorders are more common in certain age groups.

Depending on the disease to be treated and the subject's condition, Compound A or Compound B provided herein may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Compound A or Compound B provided herein may be formulated, alone or together, in suitable dosage unit with pharmaceutically acceptable excipients, carriers, adjuvants and vehicles, appropriate for each route of administration.

In one embodiment, Compound A or Compound B provided herein is administered orally.

In another embodiment, Compound A or Compound B provided herein is administered parenterally. In certain embodiments, an aqueous solution containing Compound A or Compound B provided herein is administered parenterally.

In yet another embodiment, Compound A or Compound B provided herein is administered intravenously. In certain embodiments, an aqueous solution containing Compound A or Compound B provided herein is administered intravenously.

Compound A or Compound B provided herein can be delivered as a single dose such as, e.g., a single bolus injection, or oral tablets or pills; or over time, such as, e.g., continuous infusion over time or divided bolus doses over time. Compound A or Compound B provided herein can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92 (3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound A or Compound B provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound A or Compound B provided herein, is administered once or more than once each day, for example, for a period of time. The term "continuous" is intended to mean that a therapeutic compound, such as Compound A or Compound B provided herein, is administered daily for an uninterrupted period of at least 10 days to 52 weeks. The term "intermittent" or "intermittently" as used herein is intended to mean stopping and starting at either regular or irregular intervals. For example, intermittent administration of Compound A or Compound B provided herein is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound A or Compound B provided herein is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound A or Compound B provided herein is administered once a day. In another embodiment, Compound A or Compound B provided herein is administered twice a day. In yet another embodiment, Compound A or Compound B provided herein, is administered three times a day. In still another embodiment, Compound A or Compound B provided herein is administered four times a day.

In certain embodiments, Compound A or Compound B provided herein is administered once per day from one day to six months, from one week to three months, from one week to four weeks, from one week to three weeks, or from one week to two weeks. In certain embodiments, Compound A or Compound B provided herein is administered once per day for one week, two weeks, three weeks, or four weeks. In one embodiment, Compound A or Compound B provided herein is administered once per day for 4 days. In one embodiment, Compound A or Compound B provided herein is administered once per day for 5 days. In one embodiment, Compound A or Compound B provided herein, is administered once per day for 6 days. In one embodiment, Compound A or Compound B provided herein is administered once per day for one week. In another embodiment, Compound A or Compound B provided herein is administered once per day for two weeks. In yet another embodiment, Compound A or Compound B provided herein is administered once per day for three weeks. In still another embodiment, Compound A or Compound B provided herein is administered once per day for four weeks.

5.3.1. Combination Therapy with a Second Active Agent

Compound A or Compound B provided herein can also be combined or used in combination with other therapeutic agents useful in the treatment and/or prevention of cancer described herein.

In one embodiment, provided herein is a method of treating, preventing, or managing cancer, comprising administering to a patient Compound A or Compound B provided herein in combination with one or more second active agents, and optionally in combination with radiation therapy, blood transfusions, or surgery. Examples of second active agents are disclosed herein (see, e.g., section 5.4). For example, Compound A or Compound B may be used in combination with one or more second active agents in a method of treating cancer.

Compound A or Compound B provided herein can also be combined or used in combination with other therapeutic agents useful in the treatment and/or prevention of MDS described herein.

In one embodiment, provided herein is a method of treating, preventing, and/or managing MDS, comprising administering to a patient Compound A or Compound B provided herein in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, e.g., Compound A or Compound B can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of Compound A or Compound B provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound A or Compound B is independent of the route of administration of a second therapy. In one embodiment, Compound A or Compound B is administered orally. In another embodiment, Compound A or Compound B is administered intravenously. Thus, in accordance with these embodiments, Compound A or Compound B provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound A or Compound B provided herein and a second therapy are administered by the same mode of administration, orally or by IV. In another embodiment, Compound A or Compound B provided herein is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of Compound A or Compound B provided herein and any optional additional active agents concurrently administered to the patient.

One or more second active ingredients or agents can be used together with Compound A or Compound B in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with Compound A or Compound B provided herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with Compound A or Compound B include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Compound A or Compound B can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3 (1):77-84 (2001).

Second active agents that are small molecules can also be used to alleviate adverse effects associated with the administration of Compound A or Compound B provided herein. However, like some large molecules, many are believed to be capable of providing a synergistic effect when administered with (e.g., before, after or simultaneously) Compound A or Compound B provided herein. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol;

mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, Compound A or Compound B is administered in combination with checkpoint inhibitors. In one embodiment, one checkpoint inhibitor is used in combination with Compound A or Compound B in connection with the methods provided herein. In another embodiment, two checkpoint inhibitors are used in combination with Compound A or Compound B in connection with the methods provided herein. In yet another embodiment, three or more checkpoint inhibitors are used in combination with Compound A or Compound B in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., J. Immunol., 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., Clin. Cancer Res., 2012, 3834).

In one embodiment, the checkpoint inhibitors is a TIM3 (T-cell immunoglobulin domain and mucin domain 3) inhibitor (Fourcade et al., J. Exp. Med., 2010, 207, 2175-86; Sakuishi et al., J. Exp. Med., 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with second active agents as described herein where appropriate for treating diseases described herein and understood in the art.

In certain embodiments, Compound A or Compound B can be used in combination with one or more immune cells expressing one or more chimeric antigen receptors (CARs) on their surface (e.g., a modified immune cell). Generally, CARs comprise an extracellular domain from a first protein e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a VL linked to VH by a flexible linker, wherein said VL and VH are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin $\alpha v \beta 3$ (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ES0-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pm1-RAR$\alpha$ fusion protein, PTPRK, K-ras, N-ras, triosephosphate isomerase, Gage 3, 4, 5, 6, 7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, Leukemia (2012), 26, 2186-2196. Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 105(11):4247-4254 (2005).

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Compound A or Compound B In certain embodiments of the methods provided herein, use of a second active agent in combination with provided herein may be modified or delayed during or shortly following administration of Compound A or Compound B provided herein as deemed appropriate by the practitioner of skill in the art. In certain embodiments, subjects being administered Compound A or Compound B provided herein alone or in combination with other therapies may receive supportive care including antiemetics, myeloid growth factors, and transfusions of platelets, when appropriate. In some embodiments, subjects being administered provided herein may be administered a growth factor as a second active agent according to the judgment of the practitioner of skill in the art. In some embodiments, provided is administration of Compound A or Compound B provided herein in combination with erythropoietin or darbepoetin (Aranesp).

In certain embodiments, Compound A or Compound B provided herein is administered with gemcitabine, cisplatinum, 5-fluorouracil, mitomycin, methotrexate, vinblastine, doxorubicin, carboplatin, thiotepa, paclitaxel or docetaxel to patients with locally advanced or metastatic transitional cell bladder cancer.

In certain embodiments, Compound A or Compound B provided herein is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, Compound A or Compound B provided herein is administered with methotrexate, cyclophosphamide, 5-fluorouracil, taxane, everolimus, abraxane, lapatinib, herceptin, pamidronate disodium, eribulin mesylate, everolimus, gemcitabine, palbociclib, ixabepilone, kadcyla, pertuzumab, theotepa, aromatase inhibitors, exemestane, selective estrogen modulators, estrogen receptor antagonists, anthracyclines, emtansine, and/or pexidartinib to patients with metastatic breast cancer.

In certain embodiments, Compound A or Compound B provided herein is administered with temozolomide, doxorubicin (Adriamycin), fluorouracil (Adrucil, 5-fluorouracil), or streptozocin (Zanosar) to patients with neuroendocrine tumors.

In certain embodiments, Compound A or Compound B provided herein is administered with methotrexate, gemcitabine, cisplatin, cetuximab, 5-fluorouracil, bleomycin, docetaxel or carboplatin to patients with recurrent or metastatic head or neck cancer.

In certain embodiments, Compound A or Compound B provided herein is administered with gemcitabine, abraxane, 5-fluorouracil, afinitor, irinotecan, mitomycin C, sunitinib or tarceva to patients with pancreatic cancer.

In certain embodiments, Compound A or Compound B provided herein is administered to patients with colon cancer in combination with ARISA®, avastatin, oxaliplatin, 5-fluorouracil, irinotecan, capecitabine, cetuximab, ramucirumab, panitumumab, bevacizumab, leucovorin calcium, lonsurf, regorafenib, ziv-aflibercept, taxol, and/or taxotere.

In certain embodiments, Compound A or Compound B provided herein is administered with capecitabine and/or vemurafenib to patients with refractory colorectal cancer or patients who fail first line therapy or have poor performance in colon or rectal adenocarcinoma.

In certain embodiments, Compound A or Compound B provided herein is administered in combination with fluorouracil, leucovorin, and irinotecan to patients with Dukes C & D colorectal cancer or to patients who have been previously treated for metastatic colorectal cancer.

In certain embodiments, Compound A or Compound B provided herein is administered to patients with refractory colorectal cancer in combination with capecitabine, xeloda, and/or irinotecan.

In certain embodiments, Compound A or Compound B provided herein is administered with capecitabine and irinotecan to patients with refractory colorectal cancer or to patients with unresectable or metastatic colorectal carcinoma.

In certain embodiments, Compound A or Compound B provided herein is administered alone or in combination with interferon alpha or capecitabine to patients with unresectable or metastatic hepatocellular carcinoma; or with cisplatin and thiotepa, or with sorafenib tosylate to patients with primary or metastatic liver cancer.

In certain embodiments, Compound A or Compound B provided herein is administered in combination with doxorubicin, paclitaxel, vinblastine or pegylated interferon alpha to patients with Kaposi's sarcoma.

In certain embodiments, Compound A or Compound B provided herein is administered in combination with arsenic trioxide, fludarabine, carboplatin, daunorubicin, cyclophosphamide, cytarabine, doxorubicin, idarubicin, mitoxantrone hydrochloride, thioguanine, vincritine, and/or topotecan to patients with refractory or relapsed or high-risk acute myeloid leukemia.

In certain embodiments, Compound A or Compound B provided herein is administered in combination with liposomal daunorubicin, topotecan and/or cytarabine to patients with unfavorable karotype acute myeloblastic leukemia.

In certain embodiments, Compound A or Compound B provided herein is administered in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, abraxane, erlotinib, gefitinib, and/or irinotecan to patients with non-small cell lung cancer.

In certain embodiments, Compound A or Compound B provided herein is administered in combination with carboplatin and irinotecan to patients with non-small cell lung cancer.

In certain embodiments, Compound A or Compound B provided herein is administered with doxetaxol to patients with non-small cell lung cancer who have been previously treated with carbo/etoposide and radiotherapy.

In certain embodiments, Compound A or Compound B provided herein is administered in combination with carboplatin and/or taxotere, or in combination with carboplatin, pacilitaxel and/or thoracic radiotherapy to patients with non-small cell lung cancer.

In certain embodiments, Compound A or Compound B provided herein is administered in combination with taxotere to patients with stage IIIB or IV non-small cell lung cancer.

In certain embodiments, Compound A or Compound B provided herein is administered in combination with oblimersen (Genasense®), methotrexate, mechlorethamine hydrochloride, etoposide, topotecan or doxorubicin to patients with small cell lung cancer.

In certain embodiments, Compound A or Compound B provided herein is administered in combination with ABT-737 (Abbott Laboratories) and/or obatoclax (GX15-070) to patients with lymphoma and other blood cancers.

In certain embodiments, Compound A or Compound B provided herein is administered alone or in combination with a second active ingredient such as vinblastine, fludarabine adcetris, ambochlorin, becenum, bleomycin, brentuximab vedotin, carmustinem chlorambucil, cyclophosphamide, dacarbazine, doxorubicin, lomustine, matulane, mechlorethamine hydrochloride, prednisone, procarbazine hydrochloride or vincristine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, Compound A or Compound B provided herein is administered in combination with taxotere, dabrafenib, imlygic, ipilimumab, pembrolizumab, nivolumab, trametinib, vemurafenib, talimogene laherparepvec, IL-2, IFN, GM-CSF, and/or dacarbazine to patients with various types or stages of melanoma.

In certain embodiments, Compound A or Compound B provided herein is administered alone or in combination with vinorelbine to patients with malignant mesothelioma, or stage IIIB non-small cell lung cancer with pleural implants or malignant pleural effusion mesothelioma syndrome.

In certain embodiments, Compound A or Compound B provided herein is administered to patients with various types or stages of multiple myeloma in combination with dexamethasone, zoledronic acid, palmitronate, GM-CSF, biaxin, vinblastine, melphalan, busulphan, cyclophosphamide, IFN, prednisone, bisphosphonate, celecoxib, arsenic trioxide, PEG INTRON-A, vincristine, becenum, bortezomib, carfilzomib, doxorubicin, panobinostat, lenalidomide, pomalidomide, thalidomide, mozobil or a combination thereof.

In certain embodiments, Compound A or Compound B provided herein is administered to patients with various types or stages of multiple myeloma in combination with chimeric antigen receptor (CAR) T-cells.

In certain embodiments, Compound A or Compound B provided herein is administered to patients with relapsed or refractory multiple myeloma in combination with doxorubicin (Doxil®), vincristine and/or dexamethasone (Decadron®).

In certain embodiments, Compound A or Compound B provided herein is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, avastin, cyclophosphamide, topotecan, olaparib, thiotepa, or a combination thereof.

In certain embodiments, Compound A or Compound B provided herein is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon, zytiga, bicalutamide, cabazitaxel, degarelix, enzalutamide, zoladex, leuprolide acetate, mitoxantrone hydrochloride, prednisone, sipuleucel-T, radium 223 dichloride, or a combination thereof.

In certain embodiments, Compound A or Compound B provided herein is administered to patients with various types or stages of renal cell cancer, in combination with capecitabine, IFN, tamoxifen, IL-2, GM-CSF, Celebrex®, or a combination thereof.

In certain embodiments, Compound A or Compound B provided herein is administered to patients with various types or stages of gynecologic, uterus or soft tissue sarcoma cancer in combination with IFN, dactinomycin, doxorubicin, imatinib mesylate, pazopanib, hydrochloride, trabectedin, a COX-2 inhibitor such as Celebrex®, and/or sulindac.

In certain embodiments, Compound A or Compound B provided herein is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, Compound A or Compound B provided herein is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

In certain embodiments, Compound A or Compound B provided herein is administered to patients with MDS in combination with azacitidine, cytarabine, daunorubicin, decitabine, idarubicin, lenalidomide or a combination thereof.

Also encompassed herein is a method of increasing the dosage of an anti-cancer drug or agent that can be safely and effectively administered to a patient, which comprises administering to the patient (e.g., a human) Compound A or Compound B provided herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of Compound A or Compound B provided herein alleviates or reduces adverse effects which are of such severity that it would otherwise limit the amount of anti-cancer drug.

In one embodiment, Compound A or Compound B provided herein is administered daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, Compound A or Compound B provided herein is administered in combination with specific agents such as heparin, aspirin, coumarin, or G-CSF to avoid adverse effects that are associated with anti-cancer drugs such as but not limited to neutropenia or thrombocytopenia.

In one embodiment, Compound A or Compound B provided herein is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering Compound A or Compound B of provided herein in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that Compound A or Compound B provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. Compound A or Compound B provided herein and other active ingredient can be administered to a patient prior to, during, or after the occurrence of the adverse effect associated with conventional therapy.

In one embodiment, the compound provided herein can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

In certain embodiments, the methods provided herein comprise administration of calcium, calcitriol, and vitamin D supplementation with Compound A or Compound B. In certain embodiments, the methods provided herein comprise administration of calcium, calcitriol, and vitamin D supplementation prior to the treatment with Compound A or Compound B.

In certain embodiments, calcium supplementation is administered to deliver at least 1200 mg of elemental calcium per day given in divided doses. In certain embodiments, calcium supplementation is administered as calcium carbonate in a dose of 500 mg administered three times a day per orally (PO).

In certain embodiments, calcitriol supplementation is administered to deliver 0.25 µg calcitriol (PO) once daily.

In certain embodiments, vitamin D supplementation is administered to deliver about 500 IU to about 5000 IU vitamin D once daily. In certain embodiments, vitamin D supplementation is administered to deliver about 1000 IU vitamin D once daily. In certain embodiments, vitamin D supplementation is administered to deliver about 50,000 IU vitamin D weekly. In certain embodiments, vitamin D supplementation is administered to deliver about 1000 IU vitamin D2 or D3 once daily. In certain embodiments, vitamin D supplementation is administered to deliver about 50,000 IU vitamin D2 or D3 weekly.

In certain embodiments, Compound A or Compound B provided herein and doxetaxol are administered to patients with non-small cell lung cancer who were previously treated with carbo/VP 16 and radiotherapy.

5.3.2. Use with Transplantation Therapy

Compound A or Compound B provided herein can be used to reduce the risk of Graft Versus Host Disease (GVHD). Therefore, encompassed herein is a method of treating, preventing and/or managing cancer, which comprises administering Compound A or Compound B provided herein in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of Compound A or Compound B provided herein and transplantation therapy provides a unique and unexpected synergism. In particular, Compound A or Compound B provided herein exhibits immunomodulatory activity that may provide additive or synergistic effects when given concurrently with transplantation therapy in patients with cancer.

Compound A or Compound B provided herein can work in combination with transplantation therapy reducing complications associated with the invasive procedure of transplantation and risk of GVHD. Encompassed herein is a method of treating, preventing and/or managing cancer which comprises administering to a patient (e.g., a human) Compound A or Compound B provided herein before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, Compound A or Compound B provided herein is administered to patients with acute myeloid leukemia (AML) before, during, or after transplantation.

In one embodiment, Compound A or Compound B provided herein is administered to patients with multiple myeloma before, during, or after the transplantation of autologous peripheral blood progenitor cell.

In one embodiment, Compound A or Compound B provided herein is administered to patients with NHL (e.g., DLBCL) before, during, or after the transplantation of autologous peripheral blood progenitor cell.

5.3.3. Cycling Therapy

In certain embodiments, Compound A or Compound B provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, Compound A or Compound B provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of Compound A or Compound B provided herein for more cycles than are typical when it is administered alone. In certain embodiments, Compound A or Compound B provided herein is administered for a greater number of cycles that would typically cause dose-limiting toxicity in a patient to whom a second active ingredient is not also being administered.

In one embodiment, Compound A or Compound B provided herein is administered daily and continuously for three or four weeks at a dose of from about 0.1 to about 150 mg/d followed by a break of one or two weeks.

In another embodiment, Compound A or Compound B and a second active ingredient are administered orally, with administration of the compound occurring 30 to 60 minutes prior to a second active ingredient, during a cycle of four to six weeks. In certain embodiments, the combination of Compound A or Compound B and a second active ingredient is administered by intravenous infusion over about 90 minutes every cycle. In certain embodiments, one cycle comprises the administration from about 0.1 to about 150 mg/day of Compound A or Compound B and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

5.4. Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with Compound A or Compound B provided herein, alone or in combination with a second active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

Also encompassed are methods of treating subjects having relapsed or refractory leukemia. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the methods provided herein are used to treat drug resistant leukemias, such as chronic myelogenous leukemia (CML). Thus, treatment with Compound A or Compound B provided herein could provide an alternative for patients who do not respond to other methods of treatment. In some embodiments, such other methods of treatment encompass treatment with Gleevec® (imatinib mesylate). In some embodiments, provided herein are methods of treatment of Philadelphia chromosome positive chronic myelogenous leukemia (Ph+CML). In some embodiments, provided herein are methods of treatment of Gleevec® (imatinib mesylate) resistant Philadelphia chromosome positive chronic myelogenous leukemia (Ph+CML).

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembelic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

5.5. Formulation of Pharmaceutical Compositions

The pharmaceutical compositions provided herein contain therapeutically effective amounts of one or more compounds provided herein and a pharmaceutically acceptable carrier, diluent or excipient.

In one embodiment, the pharmaceutical compositions provided herein comprise Compound A or Compound B provided herein and one or more pharmaceutically acceptable excipients or carriers.

Compound A or Compound B provided herein can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically Compound A and/or Compound B described above is formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds provided herein is mixed with a suitable pharmaceutical carrier or vehicle. In certain embodiments, the concentrations of Compound A or Compound B provided herein are effective for delivery of an amount, upon administration, that treats, prevents, or ameliorates one or more of the symptoms and/or progression of cancer, including solid tumors and blood borne tumors.

Typically, the compositions are formulated for single dosage administration. To formulate a composition, the weight fraction of Compound A or Compound B provided herein is dissolved, suspended, dispersed or otherwise mixed in a selected vehicle at an effective concentration such that the treated condition is relieved or ameliorated. Pharmaceutical carriers or vehicles suitable for administration of Compound A or Compound B provided herein include any such carriers known to those skilled in the art to be suitable for the particular mode of administration.

In addition, Compound A or Compound B provided herein may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of Compound A or Compound B provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Compound A or Compound B provided herein is included in the pharmaceutically acceptable carrier in an amount sufficient to exert a therapeutically useful effect in the absence of undesirable side effects on the patient treated. The therapeutically effective concentration may be determined empirically by testing Compound A or Compound B provided herein in in vitro and in vivo systems described herein and then extrapolated therefrom for dosages for humans.

The concentration of Compound A or Compound B provided herein in the pharmaceutical composition will depend on absorption, tissue distribution, inactivation and excretion rates of the compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of Compound A or Compound B provided herein are mixed with a suitable pharmaceutical carrier or vehicle for systemic, topical or local administration to form pharmaceutical compositions. Compound A or Compound B provided herein are included in an amount effective for ameliorating one or more symptoms of, or for treating, retarding progression, or preventing. The concentration of Compound A or Compound B provided herein in the composition will depend on absorption, tissue distribution, inactivation, excretion rates of the compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which Compound A or Compound B provided herein exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of Compound A or Compound B provided herein. Compound A or Compound B provided herein are formulated and administered in unit dosage forms or multiple dosage forms. Unit dose forms as used herein refer to physically discrete units suitable for human and animal subjects and packaged individually as is known in the art. Each unit dose contains a predetermined quantity of Compound A or Compound B provided herein sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing Compound A or Compound B provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing Compound A or Compound B provided herein in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

Compound A or Compound B provided herein may be prepared with carriers that protect the compound against rapid elimination from the body, such as time release formulations or coatings.

The compositions may include other active compounds to obtain desired combinations of properties. Compound A or Compound B provided herein may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing Compound A or Compound B provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

5.5.1. Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, Compound A or Compound B provided herein could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. Compound A or Compound B provided herein can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is Compound A or Compound B as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing Compound A or Compound B provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

5.5.2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, Compound A or Compound B provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing Compound A or Compound B provided herein is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of Compound A or Compound B provided herein to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

Compound A or Compound B provided herein may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

5.5.3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving Compound A or Compound B provided herein in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound provided herein. Such amount can be empirically determined.

5.5.4. Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

Compound A or Compound B provided herein may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will have diameters of less than 50 microns or less than 10 microns.

Compound A or Compound B provided herein may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5.5.5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

5.5.6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

5.5.7. Targeted Formulations

Compound A or Compound B provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of Compound A or Compound B provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

5.5.8. Articles of Manufacture

Compound A or Compound B provided herein which is used for treatment, prevention or amelioration of one or more symptoms or progression of cancer, including solid tumors and blood borne tumors, and a label that indicates that the compound is used for treatment, prevention or amelioration of one or more symptoms or progression of cancer, including solid tumors and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

5.6. Evaluation of Activity

Standard physiological, pharmacological and biochemical procedures are available for testing the compounds to identify those that possess the desired anti-proliferative activity. Such assays include, for example, biochemical assays such as binding assays, radioactivity incorporation assays, as well as a variety of cell based assays, including KG-1 cell proliferation assay described in the Example section.

5.7. Preparation of Compounds

Compound A or Compound B provided herein can be prepared by methods known to one of skill in the art and following procedures similar to those described in the Examples section herein and routine modifications thereof.

6. EXAMPLES

The following Examples are presented by way of illustration, not limitation. The following abbreviations are used in descriptions and examples.

Example 1

Preparation of (3-(5-((2,2-difluoro-2-(4-fluorophenyl)acetamido)methyl)-1-oxoisoindolin-2-yl)-2,6-dioxopiperidin-1-yl)methyl Dihydrogen Phosphate

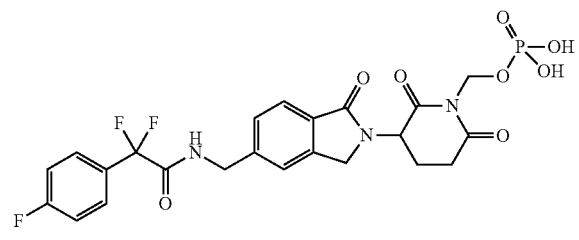 [SMILES: O=C1CCC(N2Cc3cc(CNC(=O)C(F)(F)c4ccc(F)cc4)ccc3C2=O)C(=O)N1COP(=O)(O)O]

A. Methyl 4-bromo-2-methylbenzoate

4-Bromo-2-methylbenzoic acid (100 g, 465.02 mmol), concentrated sulfuric acid (52 mL) in methanol (1 L) were combined and heated to 65° C. for 18 hours. The reaction was concentrated and the residue diluted with ethyl acetate (500 mL), washed with saturated sodium bicarbonate solution (150 mL), water (200 mL), and brine (250 mL) and dried over sodium sulfate. The organic phase was concentrated under reduced pressure and further dried under high vacuum to give methyl 4-bromo-2-methylbenzoate (102 g, 445.27 mmol, 95% yield) as a red liquid. 1H NMR (400 MHz, Chloroform-d1) δ 7.78 (d, J=8.3 Hz, 1H), 7.45-7.30 (m, 2H), 3.88 (s, 3H), 2.57 (s, 3H).

B. Methyl-4-bromo-2-(bromomethyl) benzoate

Methyl 4-bromo-2-methylbenzoate (102 g, 445.27 mmol), NBS (79.2 g, 445.27 mmol), Azo-isobutyronitrile (2.58 g, 16 mmol) in acetonitrile (600 mL) were combined and refluxed at 85° C. for 18 hours. The mixture was concentrated, and to the residue was added dichloromethane (150 mL). The resultant solid was removed by filtration. The filtrate was concentrated and purified by flash column chromatography (0-4% EtOAc in Hexanes). Fractions containing product was concentrated under reduced pressure and further dried under high vacuum to give Methyl-4-bromo-2-(bromomethyl) benzoate (100 g, 324.70 mmol, 72.9% yield) as an off-white solid. 1H NMR (300 MHz, Dimethylsulfoxide-d$_6$) δ 7.88 (d, J=2.2 Hz, 1H), 7.82 (dd, J=8.4, 2.1 Hz, 1H), 7.72-7.64 (m, 1H), 5.00 (s, 2H), 3.88 (s, 3H).

C. 3-(5-Bromo-1-oxoisoindolin-2-yl)piperidine-2,6-dione

Methyl-4-bromo-2-(bromomethyl) benzoate (100 g, 324.70 mmol), 3-Aminopiperidine-2,6-dione.hydrochloride (53.2 g, 324.70 mmol), triethylamine (113.29 mL, 811.75 mmol), and dry dimethylformamide (400 mL) were combined and stirred at room temperature under inert atmosphere for 18 hours. The reaction was cooled to 5° C. and diluted with water (400 mL), acetic acid (115 mL), diethylether (300 mL) with continued stirring at room temperature for 2 hours. The resultant solid was filtered, washed with ether (100 mL) and further dried under high vacuum to give 3-(5-Bromo-1-oxoisoindolin-2-yl)piperidine-2,6-dione (46 g, 142.35 mmol, 43.8% yield) as a light blue solid. MS (ESI) m/z 325.0 [M+1]$^+$.

D. 2-(2,6-Dioxopiperidin-3-yl)-1-oxoisoindoline-5-carbonitrile 3-(5-Bromo-1-oxoisoindolin-2-yl)piperidine-2,6-dione (46 g, 142.35 mmol), 1,1'-Bis(diphenylphosphino)ferrocene (788 mg, 1.423 mmol), zinc cyanide (25 g, 213.52 mmol), zinc acetate (7.83 g, 42.7 mmol) and dry dimethylformamide (360 mL) were combined and degassed before addition of tris(dibenzylideneacetone)dipalladium(0) (0.364 g, 0.398 mmol). The mixture was evacuated and replaced with argon 3 times, then stirred at 120° C. for 20 hours. The mixture was cooled to room temperature, filtered and purified by silica column chromatography (0-5% methanol in dichloromethane). Fractions containing product were combined and solvent removed under reduced pressure and then further dried under high vacuum to give 2-(2,6-dioxopiperidin-3-yl)-1-oxoisoindoline-5-carbonitrile (22 g, 81.78 mmol, 57.2% yield) as a brown solid. MS (ESI) m/z 268.0 [M-H$^+$].

E. 3-(5-(Aminomethyl)-1-oxoisoindolin-2-yl)piperidine-2,6-dione 2-(2,6-Dioxopiperidin-3-yl)-1-oxoisoindoline-5-carbonitrile (10 g, 37.13 mmol), methanesulfonic acid (2.6 mL, 40.85 mmol), 10% dry Palladium on carbon (4 g) and dimethylacetamide (320 mL) were combined and shaken in a hydrogenation vessel and kept under 50 Psi at 40° C. for 20 hours. The hydrogen atmosphere was evacuated and the mixture was filtered through a celite pad, washed with water (100 mL), and concentrated. To the resulting residue was added 1% methanol-dichloromethane which upon filtration and drying under high vacuum to provide 3-(5-(aminomethyl)-1-oxoisoindolin-2-yl)piperidine-2,6-dione (5.6 g, 15.17 mmol, 40% yield) as an off-white solid. MS (ESI) m/z 272.0 [M−1].

F. N-((2-(2,6-dioxopiperidin-3-yl)-1-oxoisoindolin-5-yl)methyl)-2,2-difluoro-2-(4-fluorophenyl)acetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(4-fluorophenyl)acetic acid (0.103 g, 0.541 mmol) followed by N-ethyl-N-isopropylpropan-2-amine (0.262 ml, 1.624 mmol). The mixture was stirred at 25° C. for 16 hours. Thirty (30) mL of water was added, and the resulting mixture was filtered. Filtrate was rinsed with EtOAc, dried under vacuum to afford N-((2-(2,6-dioxopiperidin-3-yl)-1-oxoisoindolin-5-yl)methyl)-2,2-difluoro-2-(4-fluorophenyl)acetamide (0.100 g, 0.225 mmol, 41.5% yield) as a white solid. $^1$H NMR (500 MHz, DMSO-d$_6$) δ ppm 10.98 (br. s., 1H) 9.66 (t, J=5.99 Hz, 1H) 7.58-7.73 (m, 3H) 7.29-7.47 (m, 4H) 5.11 (dd, J=13.40, 5.20 Hz, 1H) 4.38-4.53 (m, 3H) 4.24-4.36 (m, 1H) 2.81-3.00 (m, 1H) 2.56-2.67 (m, 1H) 2.40 (qd, J=13.19, 4.57 Hz, 1H) 1.91-2.07 (m, 1H).

G. Di-tert-butyl ((3-(5-((2,2-difluoro-2-(4-fluorophenyl)acetamido)methyl)-1-oxoisoindolin-2-yl)-2,6-dioxopiperidin-1-yl)methyl) phosphate A mixture of N-((2-(2,6-dioxopiperidin-3-yl)-1-oxoisoindolin-5-yl)methyl)-2,2-difluoro-2-(4-fluorophenyl)acetamide (1.0 g, 2.245 mmol), cesium carbonate (2.195 g, 6.74 mmol), and potassium iodide (0.745 g, 4.49 mmol) in NMP (4 ml) was stirred at room temperature and di-tert-butyl (chloromethyl) phosphate (4.65 g, 17.96 mmol) was added. The mixture was stirred at 30° C. for 2 hours, at which point the starting material was barely detectable by LCMS. The reaction was stirred at ambient temperature overnight. After 14 hours, the reaction was diluted with DMSO and purified by preparatory HPLC (Gemini-NX C18 column; 40-85% acetonitrile in 10 mM ammonium carbonate in water) to give 1.12 g white solid that was 86% pure desired product (64.4% yield) by LCMS. This material was carried on to the next step without further purification. $^1$HNMR (500 MHz, DMSO-d$_6$) δ ppm 9.55-9.79 (m, 1H), 7.60-7.77 (m, 3H), 7.32-7.50 (m, 4H), 5.35-5.48 (m, 2H), 5.24-5.32 (m, 1H), 5.10-5.21 (m, 2H), 4.41-4.52 (m, 3H), 4.23-4.33 (m, 1H), 3.07-3.15 (m, 1H), 2.81-2.89 (m, 1H), 2.35-2.43 (m, 1H), 2.04-2.10 (m, 1H), 1.43-1.45 (m, 4H), 1.42 (s, 12H), 1.40 (s, 2H), 1.37-1.39 (m, 1H), 1.34 (s, 6H), 1.34 (s, 3H).

H. (3-(5-((2,2-Difluoro-2-(4-fluorophenyl)acetamido)methyl)-1-oxoisoindolin-2-yl)-2,6-dioxopiperidin-1-yl)methyl dihydrogen phosphate To a stirred solution of di-tert-butyl ((3-(5-((2,2-difluoro-2-(4-fluorophenyl)acetamido)methyl)-1-oxoisoindolin-2-yl)-2,6-dioxopiperidin-1-yl)methyl) phosphate (1.12 g, 1.648 mmol) in DCM (20 mL), was added trifluoroacetic acid (20 mL, 260 mmol) and the reaction stirred at ambient temperature. After 15 minutes, LCMS indicated complete conversion to the desired product. The reaction was concentrated by rotary evaporation and purified by prep-HPLC (Polar Luna column; 5-65% acetonitrile in water with 0.1% formic acid). The product containing fractions were frozen and lyophilized to give a fluffy white powder (410 mg, 0.738 mmol, 44.8% yield) that was determined to be 99.9% pure desired product by LCMS and HNMR. $^1$H NMR (500 MHz, DMSO-d6) δ 9.67 (t, J=5.99 Hz, 1H), 7.53-7.80 (m, 3H), 7.24-7.50 (m, 4H), 5.42 (d, J=7.25 Hz, 2H), 5.24 (dd, J=5.04, 13.24 Hz, 1H), 4.38-4.53 (m, 3H), 4.27-4.34 (m, 1H), 4.00-4.13 (m, 2H), 3.00-3.12 (m, 1H), 2.78-2.87 (m, 1H), 2.33-2.44 (m, 1H), 2.00-2.10 (m, 1H).

Alternatively, (3-(5-((2,2-difluoro-2-(4-fluorophenyl)acetamido)methyl)-1-oxoisoindolin-2-yl)-2,6-dioxopiperidin-1-yl)methyl dihydrogen phosphate may be prepared according to the following steps.

Steps A-F are the same as in the above method, and Step G and Step H are as follows:

G. Di-tert-butyl ((3-(5-((2,2-difluoro-2-(4-fluorophenyl)acetamido)methyl)-1-oxoisoindolin-2-yl)-2,6-dioxopiperidin-1-yl)methyl) phosphate A suspension of N-((2-(2,6-dioxopiperidin-3-yl)-1-oxoisoindolin-5-yl)methyl)-2,2-difluoro-2-(4-fluorophenyl)acetamide (2.0 g, 4.49 mmol) in DMA (45 mL) was heated at 40° C. until a clear solution was obtained (~30 sec). Solid potassium iodide (1.491 g, 8.98 mmol) and di-tert-butyl (chloromethyl) phosphate (9.29 g, 35.9 mmol) were added. The mixture was stirred at 40° C. for 5 min before sodium hydride (0.198 g, 4.94 mmol) was added in one portion. After 45 min, analysis by LCMS indicated a clean reaction with ~7% starting material remaining. After 2 h, the reaction was diluted with 300 mL EtOAc and washed with water (2×300 mL). The organic layer was diluted with hexanes (100 mL) and washed with brine (2×300 mL), dried ($Na_2SO_4$), filtered, and concentrated to give 11.3 g yellow oil that still contained 6% starting material by LCMS. HNMR and FNMR spectra of this material were consistent with the desired product along with a tiny bit of starting material, a large amount of phosphate reagent, and some EtOAc. The crude product was carried on as is in the next reaction.

H. (3-(5-((2,2-Difluoro-2-(4-fluorophenyl)acetamido)methyl)-1-oxoisoindolin-2-yl)-2,6-dioxopiperidin-1-yl)methyl dihydrogen phosphate To a stirred solution of crude di-tert-butyl ((3-(5-((2,2-difluoro-2-(4-fluorophenyl)acetamido)methyl)-1-oxoisoindolin-2-yl)-2,6-dioxopiperidin-1-yl)methyl) phosphate (3.00 g, 4.49 mmol) in DCM (20 mL) at 0° C. was added trifluoroacetic acid (20 mL, 260 mmol) and the reaction was stirred for 5 min at 0° C. and for 90 min at ambient temperature. LCMS analysis indicated 82% desired product and 6.7% N-((2-(2,6-dioxopiperidin-3-yl)-1-oxoisoindolin-5-yl)methyl)-2,2-difluoro-2-(4-fluorophenyl)acetamide (starting material from the previous reaction) along with some minor impurities. The reaction was concentrated by rotary evaporation and placed under high vacuum for 1 h. The resulting thick orange oil (8.48 g) was dissolved in EtOAc (200 mL) with sonication and allowed to stand at ambient temperature. After 90 min, a large volume of white solid precipitated. The solid was collected by vacuum filtration and washed with $Et_2O$ to give 1.738 g (67.8% yield for 2 steps) fine white powder. LCMS analysis indicated 97.3% purity. The HNMR spectra was clean and consistent with the desired product and there was no detectable TFA by FNMR. $^1$H NMR (500 MHz, DMSO-$d_6$) δ 9.67 (t, J=5.99 Hz, 1H), 7.63-7.73 (m, 3H), 7.34-7.46 (m, 4H), 5.44 (d, J=7.25 Hz, 2H), 5.25 (dd, J=5.20, 13.40 Hz, 1H), 4.42-4.49 (m, 3H), 4.28-4.34 (m, 1H), 3.58-3.89 (m, 2H), 3.08 (ddd, J=5.36, 13.48, 17.73 Hz, 1H), 2.80-2.87 (m, J=2.21, 4.10 Hz, 1H), 2.35 (br. s., 1H), 2.03-2.10 (m, 1H); $^{19}$F NMR (471 MHz, DMSO-$d_6$) δ −100.62 (s, 2F), −109.54 (s, 1F); MS (ESI) m/z 458.2 (100%) [M-PO4H2]$^+$, 556.1 (90%) [M+1]$^+$, 578.1 (15%) [M+Na]$^+$.

Example 2

Preparation of (3-(5-((2,2-difluoro-2-(4-fluorophenyl)acetamido)methyl)-1-oxoisoindolin-2-yl)-2,6-dioxopiperidin-1-yl)methyl L-valinate

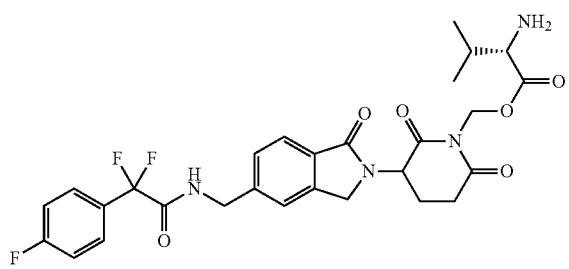 [SMILES: CC(C)[C@H](N)C(=O)OCN1C(=O)CCC(N2Cc3cc(CNC(=O)C(F)(F)c4ccc(F)cc4)ccc3C2=O)C1=O]

A. Methyl 4-bromo-2-methylbenzoate

4-Bromo-2-methylbenzoic acid (100 g, 465.02 mmol), concentrated sulfuric acid (52 mL) in methanol (1 L) were combined and heated to 65° C. for 18 hours. The reaction was concentrated and the residue diluted with ethyl acetate (500 mL), washed with saturated sodium bicarbonate solution (150 mL), water (200 mL), brine (250 mL) and dried over sodium sulfate. The organic phase was concentrated under reduced pressure and further dried under high vacuum to give methyl 4-bromo-2-methylbenzoate (102 g, 445.27 mmol, 95% yield) as a red liquid. 1H NMR (400 MHz, Chloroform-d1) δ 7.78 (d, J=8.3 Hz, 1H), 7.45-7.30 (m, 2H), 3.88 (s, 3H), 2.57 (s, 3H).

B. Methyl-4-bromo-2-(bromomethyl) benzoate

Methyl 4-bromo-2-methylbenzoate (102 g, 445.27 mmol), NBS (79.2 g, 445.27 mmol), Azo-isobutyronitrile (2.58 g, 16 mmol) in acetonitrile (600 mL) were combined and refluxed at 85° C. for 18 hours. The mixture was concentrated, and to the residue was added dichloromethane (150 mL). The resultant solid was removed by filtration. The filtrate was concentrated and purified by flash column chromatography (0-4% EtOAc in Hexanes). Fractions containing product was concentrated under reduced pressure and further dried under high vacuum to give Methyl-4-bromo-2-(bromomethyl) benzoate (100 g, 324.70 mmol, 72.9% yield) as an off-white solid. 1H NMR (300 MHz, Dimethylsulfoxide-$d_6$) δ 7.88 (d, J=2.2 Hz, 1H), 7.82 (dd, J=8.4, 2.1 Hz, 1H), 7.72-7.64 (m, 1H), 5.00 (s, 2H), 3.88 (s, 3H).

C. 3-(5-Bromo-1-oxoisoindolin-2-yl)piperidine-2,6-dione

Methyl-4-bromo-2-(bromomethyl) benzoate (100 g, 324.70 mmol), 3-Aminopiperidine-2,6-dione.hydrochloride (53.2 g, 324.70 mmol), triethylamine (113.29 mL, 811.75 mmol), and dry dimethylformamide (400 mL) were combined and stirred at room temperature under inert atmosphere for 18 hours. The reaction was cooled to 5° C. and diluted with water (400 mL), acetic acid (115 mL), diethylether (300 mL) with continued stirring at room temperature for 2 hours. The resultant solid was filtered, washed with ether (100 mL) and further dried under high vacuum to give 3-(5-Bromo-1-oxoisoindolin-2-yl)piperidine-2,6-dione (46 g, 142.35 mmol, 43.8% yield) as a light blue solid. MS (ESI) m/z 325.0 [M+1]$^+$.

D. 2-(2,6-Dioxopiperidin-3-yl)-1-oxoisoindoline-5-carbonitrile 3-(5-Bromo-1-oxoisoindolin-2-yl)piperidine-2,6-dione (46 g, 142.35 mmol), 1,1'-Bis(diphenylphosphino)ferrocene (788 mg, 1.423 mmol), zinc cyanide (25 g, 213.52 mmol), zinc acetate (7.83 g, 42.7 mmol) and dry dimethylformamide (360 mL) were combined and degassed before addition of tris(dibenzylideneacetone)dipalladium(0) (0.364 g, 0.398 mmol). The mixtures was evacuated and replaced with argon 3 times, then stirred at 120° C. for 20 hours. The mixture was cooled to room temperature, filtered and purified by silica column chromatography (0-5% methanol in dichloromethane). Fractions containing product were combined and solvent removed under reduced pressure and then further dried under high vacuum to give 2-(2,6-dioxopiperidin-3-yl)-1- oxoisoindoline-5-carbonitrile (22 g, 81.78 mmol, 57.2% yield) as a brown solid. MS (ESI) m/z 268.0 [M-H⁺].

E. 3-(5-(Aminomethyl)-1-oxoisoindolin-2-yl)piperidine-2,6-dione 2-(2,6-Dioxopiperidin-3-yl)-1-oxoisoindoline-5-carbonitrile (10 g, 37.13 mmol), methanesulfonic acid (2.6 mL, 40.85 mmol), 10% dry Palladium on carbon (4 g) and dimethylacetamide (320 mL) were combined and shaken in a hydrogenation vessel and kept under 50 Psi at 40° C. for 20 hours. The hydrogen atmosphere was evacuated and the mixture was filtered through a celite pad, washed with water (100 mL), and concentrated. To the resulting residue, was added 1% methanol-dichloromethane which upon filtration and drying under high vacuum to provide 3-(5-(aminomethyl)-1-oxoisoindolin-2-yl)piperidine-2,6-dione (5.6 g, 15.17 mmol, 40% yield) as an off-white solid. MS (ESI) m/z 272.0 [M−1].

F. N-((2-(2,6-Dioxopiperidin-3-yl)-1-oxoisoindolin-5-yl)methyl)-2,2-difluoro-2-(4-fluorophenyl)acetamide To 3-(5-(Aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(4-fluorophenyl)acetic acid (0.103 g, 0.541 mmol) followed by N-ethyl-N-isopropylpropan-2-amine (0.262 ml, 1.624 mmol). The mixture was stirred at 25° C. for 16 hours. Water (30 mL) was added, and the resulting mixture filtered. Filtrate was rinsed with EtOAc, dried under vacuum to afford N-((2-(2,6-dioxopiperidin-3-yl)-1-oxoisoindolin-5-yl)methyl)-2,2-difluoro-2-(4-fluorophenyl) acetamide (0.100 g, 0.225 mmol, 41.5% yield) as a white solid. ¹H NMR (500 MHz, DMSO-d₆) δ ppm 10.98 (br. s., 1H) 9.66 (t, J=5.99 Hz, 1H) 7.58-7.73 (m, 3H) 7.29-7.47 (m, 4H) 5.11 (dd, J=13.40, 5.20 Hz, 1H) 4.38-4.53 (m, 3H) 4.24-4.36 (m, 1H) 2.81-3.00 (m, 1H) 2.56-2.67 (m, 1H) 2.40 (qd, J=13.19, 4.57 Hz, 1H) 1.91-2.07 (m, 1H).

G. Chloromethyl (tert-butoxycarbonyl)-L-valinate (S)-2-((Tert-butoxycarbonyl)amino)-3-methylbutanoic acid (20 g, 92 mmol), sodium bicarbonate (30.9 g, 368 mmol), and tetrabutylammonium hydrogen sulfate (3.13 g, 9.21 mmol) were combined in dichloromethane (150 mL) and water (150 mL). The mixture was stirred at ambient temperature for 5 minutes. The mixture was cooled to 0° C. and chloromethyl sulfochloridate (11.17 mL, 110 mmol) was then added dropwise and the mixture allowed to stir at ambient temperature. After 2 hours, the solution was added to a separatory funnel and the aqueous was partitioned with dichloromethane (3×150 mL). The organics were combined and washed additionally with water (2×150 mL) and the organics dried over magnesium sulfate, filtered and solvent removed under reduced pressure to afford a colorless oil (28.0 g). The oil was purified via normal phase chromatography (5% ethyl acetate in hexanes) to afford a colorless oil as the title compound (24.3 g, 91 mmol, 99% yield). ¹H NMR (500 MHz, DMSO-d₆) δ 6.94-7.44 (m, 1H), 5.79-6.02 (m, 2H), 3.72-3.98 (m, 1H), 2.00 (s, 1H), 1.40 (s, 9H), 0.91 (dd, J=2.36, 6.78 Hz, 6H).

H. (3-(5-((2,2-Difluoro-2-(4-fluorophenyl)acetamido)methyl)-1-oxoisoindolin-2-yl)-2,6-dioxopiperidin-1-yl)methyl (tert-butoxycarbonyl)-L-valinate N-((2-(2,6-Dioxopiperidin-3-yl)-1-oxoisoindolin-5-yl)methyl)-2,2-difluoro-2-(4-fluorophenyl)acetamide (20 g, 44.9 mmol: Split into twenty 1 gram batches) was dissolved in hot N,N-Dimethylformamide (90 mL). To the homogeneous room temperature solution was added dropwise (S)-chloromethyl 2-((tert-butoxycarbonyl)amino)-3-methylbutanoate (13.13 g, 49.4 mmol) followed immediately by cesium carbonate (16.09 g, 49.4 mmol) and the mixture stirred at ambient temperature. After 2 hours, all of the reaction vials were combined and partitioned between 10% methanol in dichloromethane (1 L) and water (750 mL). The aqueous was partitioned additionally with dichloromethane (2×500 mL). The organics were dried over magnesium sulfate, filtered and solvent removed under reduced pressure to afford a viscous yellow liquid. The viscous liquid was diluted with 75% ethyl acetate in hexanes (1 L) and washed with water (2×500 mL) to remove dimethylformamide. The organics were dried over magnesium sulfate, filtered and solvent removed under reduced pressure to afford a yellow foam (25.05 g). The yellow foam was purified using biotage chromatography ((340 g column (100 mL/min), 0-70% ethyl acetate in hexanes (1.3 L), then 70% ethyl acetate in hexanes (3.0 L)). Pertinent fractions were combined to afford the title compound as a white foam solid (6.34 g, 9.40 mmol, 21% yield). MS(ESI) m/z 575[M-Boc]⁺.

I. (3-(5-((2,2-Difluoro-2-(4-fluorophenyl)acetamido)methyl)-1-oxoisoindolin-2-yl)-2,6-dioxopiperidin-1-yl)methyl L-valinate (2S)-(3-(5-((2,2-Difluoro-2-(4-fluorophenyl)acetamido)methyl)-1-oxoisoindolin-2-yl)-2,6-dioxopiperidin-1-yl) methyl 2-((tert-butoxycarbonyl)amino)-3-methylbutanoate (6.34 g, 9.40 mmol) was dissolved in 4.0M hydrochloric acid (117 mL, 468 mmol) in dioxanes at 0° C. The mixture was allowed to stir at 0° C. (homogeneous). After 45 minutes at 0° C., the mixture was filtered through a paper filter and washed additionally with dioxanes. The solution was condensed under reduced pressure at 38° C. water bath temperature to afford a white solid. The solid was triturated with anhydrous ethyl acetate (200 mL). The solution was then condensed under reduced pressure to afford a glassy solid (5.40 g, 8.84 mmol, 94% yield). The solid was the dissolved in pH 3 water (100 mL) and then condensed under reduced pressure. The solid was again subjected to pH 3 water (100 mL) and condensed under reduced pressure to afford the title compound (4.95 g, 8.10 mmol, 86% yield). ¹H NMR (500 MHz, DMSO-d₆) δ ppm 9.70 (t, J=5.83 Hz, 1H), 8.43 (br. s., 2H), 7.57-7.77 (m, 3H), 7.30-7.51 (m, 4H), 5.83 (dd, J=9.62, 5.52 Hz, 1H), 5.70-5.78 (m, 1H), 5.24-5.33 (m, 1H), 4.42-4.53 (m, 3H), 4.28 (t, J=17.50 Hz, 1H), 3.94 (br. s., 1H), 3.64-3.76 (m, 1H), 3.49 (dd, J=15.13, 4.73 Hz, 1H), 3.05-3.19 (m, 1H), 2.82-2.93 (m, 1H), 2.34-2.48 (m, 2H), 2.03-2.22 (m, 2H), 0.89-1.01 (m, 6H); MS(ESI) m/z 575[M]⁺.

Example 3: KG-1 Cell Proliferation Assay

The following is an example of an assay that can be used to determine the anti-proliferative activity of Compound A and Compound B in KG-1 cell line (American Type Culture Collection [ATCC]: catalogue number ATCC® CCL-246™) at 72 hours post-treatment. The seeding density for KG-1 can be optimized to ensure assay linearity in 384-well plates.

Increasing concentrations of test compounds (0.5 nM to 10 μM) was spotted in a 10-point serial dilution fashion (3-fold dilution) in duplicate via an acoustic dispenser (EDC ATS-100) into an empty 384-well plate. The dimethyl sulfoxide (DMSO) concentration was kept constant for a final assay concentration of 0.1% DMSO. Prior to testing, KG-1 cells were grown in RPMI-1640 (Roswell Park Memorial Institute-1640) medium with 10% FBS (fetal bovine serum: HyClone) and expanded in culture flasks to provide sufficient amounts of starting material. Cells were then diluted to 5000 cells per well, in a 50 μL volume and added directly to the compound-spotted 384-well plates. Cells were allowed to grow for 72 hours in 5% $CO_2$ at 37° C. At the time when exposure of cells to compound began ($t_0$), initial viable cell number was assessed via Cell Titer-Gb® Luminescent Cell Viability Assay at a 1 vol:2 vol ratio according to manufacturer's instructions (Promega Corporation, Madison, Wis.) by quantifying the level of luminescence generated by adenosine-5'-triphosphate (ATP) present in viable cells. After 72 hours, cell viability of the treated cells is assessed via Cell Titer-Glo® and read for luminescence. $IC_{50}$ values for exemplary compounds are provided in Table 1.

Activity of representative compounds is shown in Table 1, with $IC_{50}$ values as provided below:

A: 0.01 to 0.1 μM and B: >0.1 μM to 0.7 μM.

While the disclosure has been described with respect to the particular embodiments, it will be apparent to those skilled in the art that various changes and modifications may be made without departing from the spirit and scope of the disclosure as defined in the claims. Such modifications are also intended to fall within the scope of the appended claims.

All of the patents, patent applications and publications referred to herein are incorporated herein in their entireties. Citation or identification of any reference in this application is not an admission that such reference is available as prior art to this disclosure. The full scope of the disclosure is better understood with reference to the appended claims.

TABLE 1

| Compound | FCA Prolif Cell TiterGlo KG-1 72 h ($IC_{50}$) |
|---|---|
| 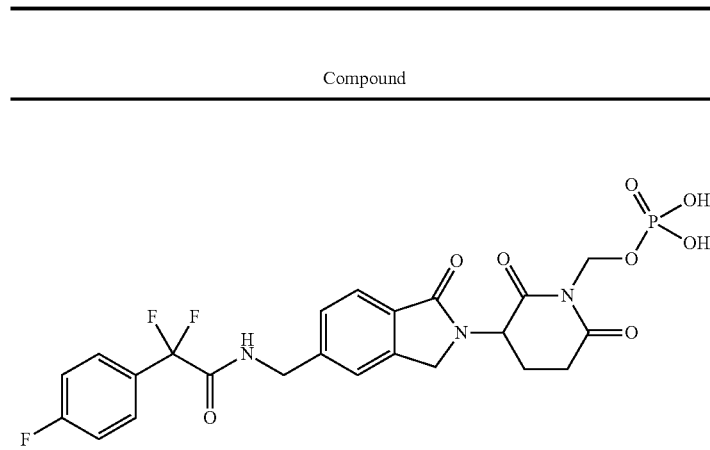 | B |
| 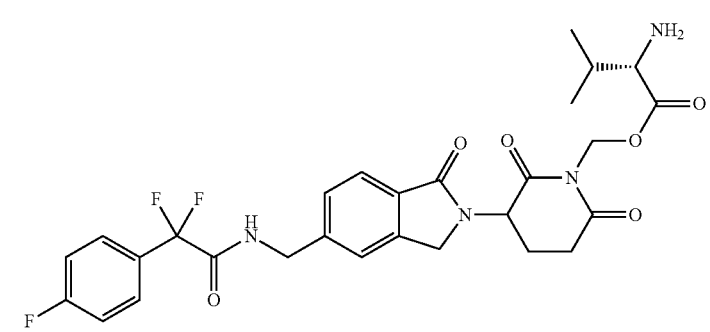 [SMILES: CC(C)[C@H](N)C(=O)OCN1C(=O)CCC(N2Cc3cc(CNC(=O)C(F)(F)c4ccc(F)cc4)ccc3C2=O)C1=O] | A |
| 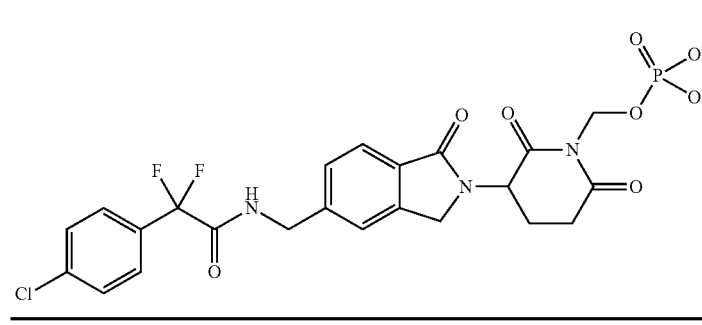 | B |

What is claimed is:

1. A compound of formula A-I:

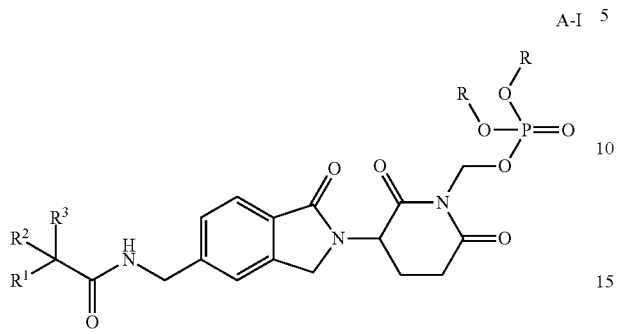

A-I or a stereoisomer or mixture of stereoisomers, tautomer, pharmaceutically acceptable salt, solvate, hydrate, co-crystal, clathrate, isotopologue or polymorph thereof, wherein:

each R is independently H, optionally substituted alkyl, or optionally substituted cycloalkyl;

$R^1$ is optionally substituted cycloalkyl, optionally substituted aryl, optionally substituted heteroaryl or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

2. The compound of claim 1, wherein the compound is of Formula A-II:

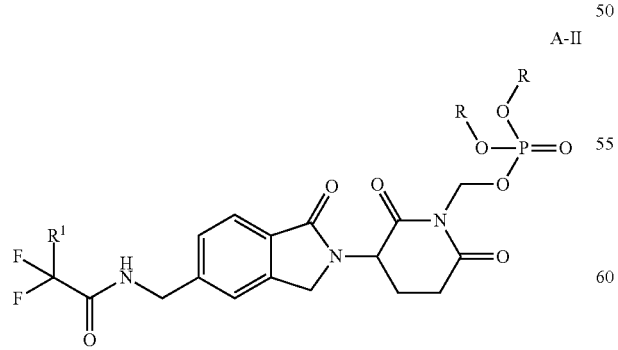

A-II or a stereoisomer or mixture of stereoisomers, tautomer, pharmaceutically acceptable salt, solvate, hydrate, co-crystal, clathrate, isotopologue or polymorph thereof, wherein:

each R is independently H, optionally substituted alkyl, or optionally substituted cycloalkyl;

$R^1$ is optionally substituted cycloalkyl, optionally substituted aryl, optionally substituted heteroaryl or optionally substituted heterocyclyl;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

3. The compound of claim 1, wherein each R is independently H or $(C_1-C_6)$alkyl; $R^1$ is optionally substituted aryl, where the substituents on $R^1$, when present, are one to three groups Q, where each Q is independently halo, alkyl, —$R^4OR^5$, —$R^4SR^5$ or $R^4OR^4C(O)N(R^6)(R^7)$; each $R^4$ is independently a direct bond or alkylene; each $R^5$ is independently hydrogen, halo, alkyl or haloalkyl; and $R^6$ and $R^7$ are each independently hydrogen or alkyl.

4. The compound of claim 1, wherein each R is independently is H or $(C_1-C_6)$alkyl; and $R^1$ is optionally substituted aryl, where the substituents on $R^1$, when present, are one to three groups Q, where each Q is independently fluoro, chloro, methyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

5. The compound of claim 1, wherein each R is independently H or $(C_1-C_6)$alkyl and $R^1$ is optionally substituted phenyl, where the substituents on $R^1$, when present, are one to three groups Q, where each Q is independently fluoro, chloro, methyl, tert butyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

6. The compound of claim 1, wherein the compound is of Formula A-III:

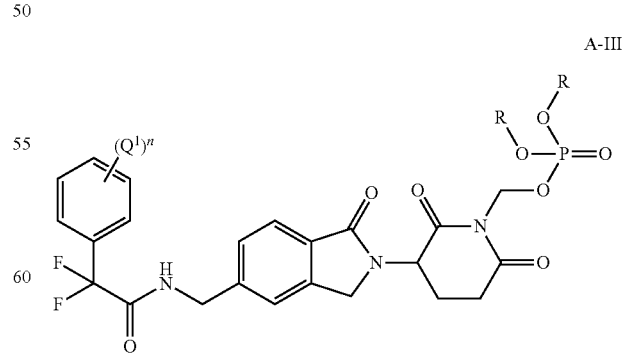

A-III or a stereoisomer or mixture of stereoisomers, tautomer, pharmaceutically acceptable salt, solvate, hydrate, co-crystal, clathrate, isotopologue or polymorph thereof, wherein:

each R is independently H, optionally substituted alkyl, or optionally substituted cycloalkyl;

each $Q^1$ is independently alkyl, halo, haloalkyl, alkoxyalkyl, hydroxyl, alkoxy, optionally substituted cycloalkyl, optionally substituted cycloalkylakyl, optionally substituted aryl —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl;

$R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl; and n is 0-3.

7. The compound of claim 1, wherein the compound is selected from the group consisting of:

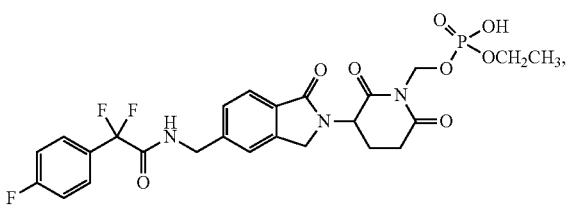

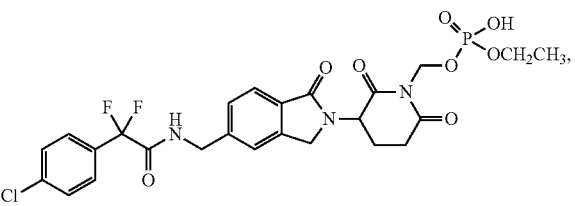

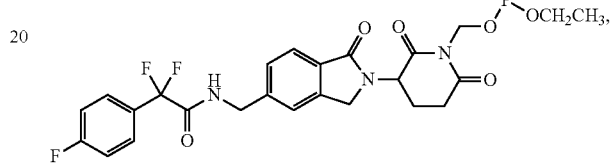

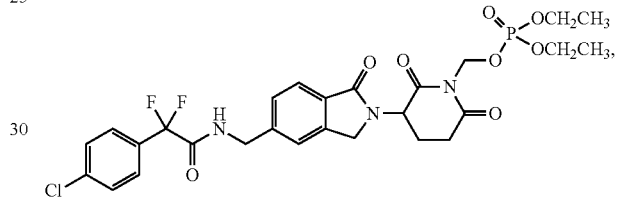

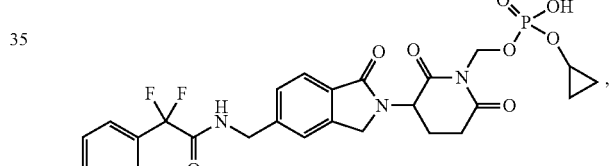

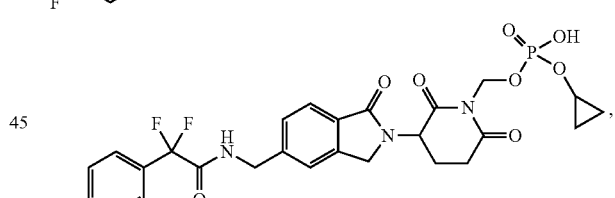

-continued

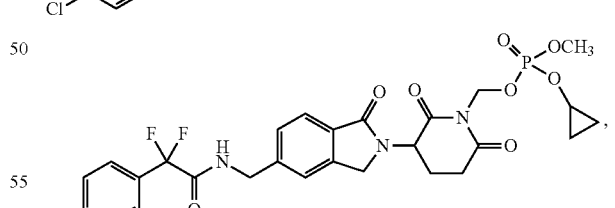

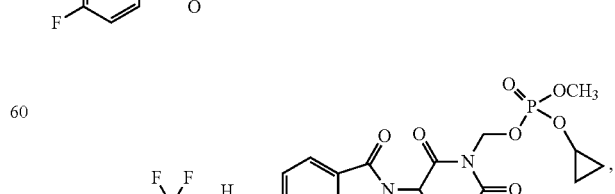

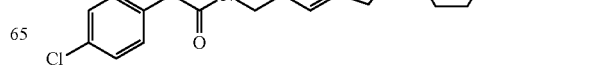

-continued

, and

[chemical structure]

[chemical structure]

8. A compound of Formula B-I:

B-I

[chemical structure]

or a stereoisomer or mixture of stereoisomers, tautomer, pharmaceutically acceptable salt, solvate, hydrate, co-crystal, clathrate, isotopologue or polymorph thereof, wherein:

each R' is independently H or optionally substituted alkyl; or optionally substituted cycloalkyl;

R' is H or optionally substituted alkyl;

$R^1$ is optionally substituted cycloalkyl, optionally substituted aryl, optionally substituted heteroaryl or optionally substituted heterocyclyl;

$R^2$ and $R^3$ are each halo;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

9. The compound of claim 8, wherein the compound is of Formula B-II:

B-II

[chemical structure]

or a stereoisomer or mixture of stereoisomers, tautomer, pharmaceutically acceptable salt, solvate, hydrate, co-crystal, clathrate, isotopologue or polymorph thereof, wherein:

each R is independently H, optionally substituted alkyl, or optionally substituted cycloalkyl;

each R' is independently is H or optionally substituted alkyl;

$R^1$ is optionally substituted cycloalkyl, optionally substituted aryl, optionally substituted heteroaryl or optionally substituted heterocyclyl;

where the substituents on $R^1$, when present are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

10. The compound of claim 8, wherein each R is independently H or ($C_1$-$C_6$)alkyl; each R' is independently is H or (C1-C6)alkyl; $R^1$ is optionally substituted aryl, where the substituents on $R^1$, when present, are one to three groups Q, where each Q is independently halo, alkyl, —$R^4OR^5$, —$R^4SR^5$ or $R^4OR^4C(O)N(R^6)(R^7)$; each $R^4$ is independently a direct bond or alkylene; each $R^5$ is independently hydrogen, halo, alkyl or haloalkyl; and $R^6$ and $R^7$ are each independently hydrogen or alkyl.

11. The compound of claim 8, wherein each R is independently H or ($C_1$-$C_6$)alkyl; each R' is independently H or (C1-C6)alkyl; $R^1$ is optionally substituted phenyl, where the substituents on $R^1$, when present, are one to three groups Q, where each Q is independently fluoro, chloro, methyl, tert butyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

12. The compound of claim 8, wherein the compound is of Formula B-III:

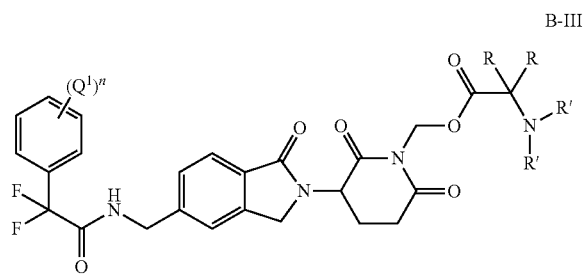

B-III or a stereoisomer or mixture of stereoisomers, tautomer, pharmaceutically acceptable salt, solvate, hydrate, co-crystal, clathrate, isotopologue or polymorph thereof, wherein:

each R is independently H, optionally substituted alkyl, or optionally substituted cycloalkyl;

each R' is independently is H or optionally substituted alkyl;

each $Q^1$ is independently alkyl, halo, haloalkyl, alkoxyalkyl, hydroxyl, alkoxy, optionally substituted cycloalkyl, optionally substituted cycloalkylakyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl or hydroxyalkyl;

$R^6$ and $R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl; and n is 0-3.

13. The compound of claim 8, wherein the compound is selected from the group consisting of:

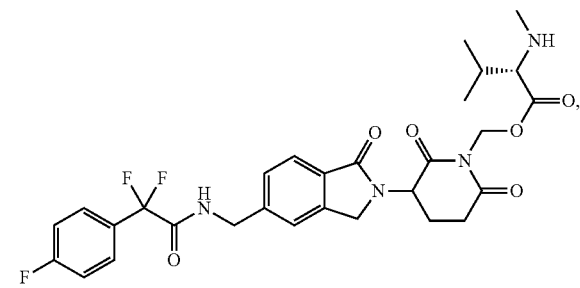

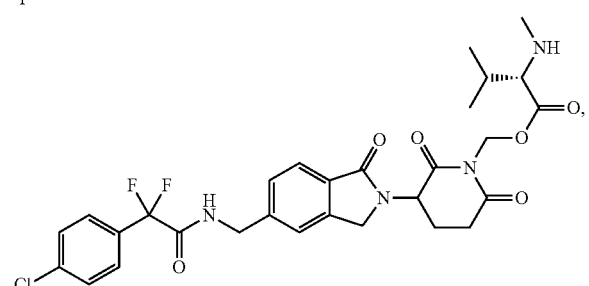

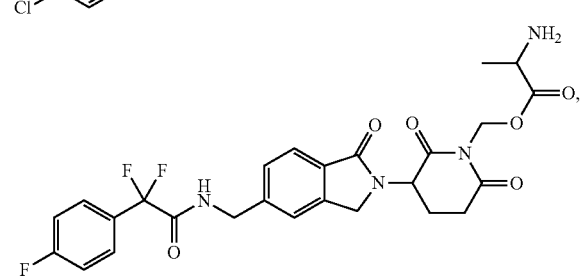

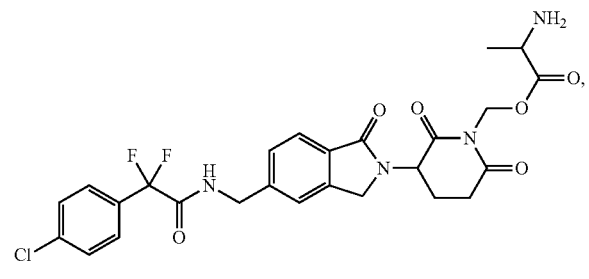

91
-continued

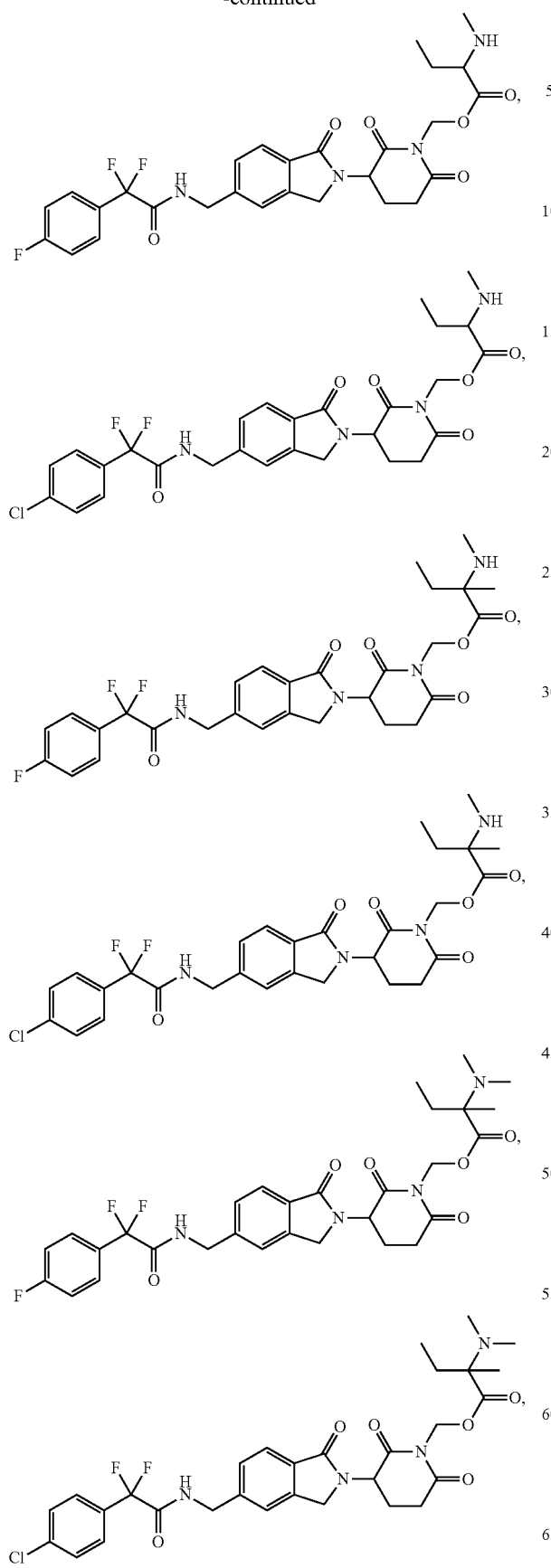

92
-continued

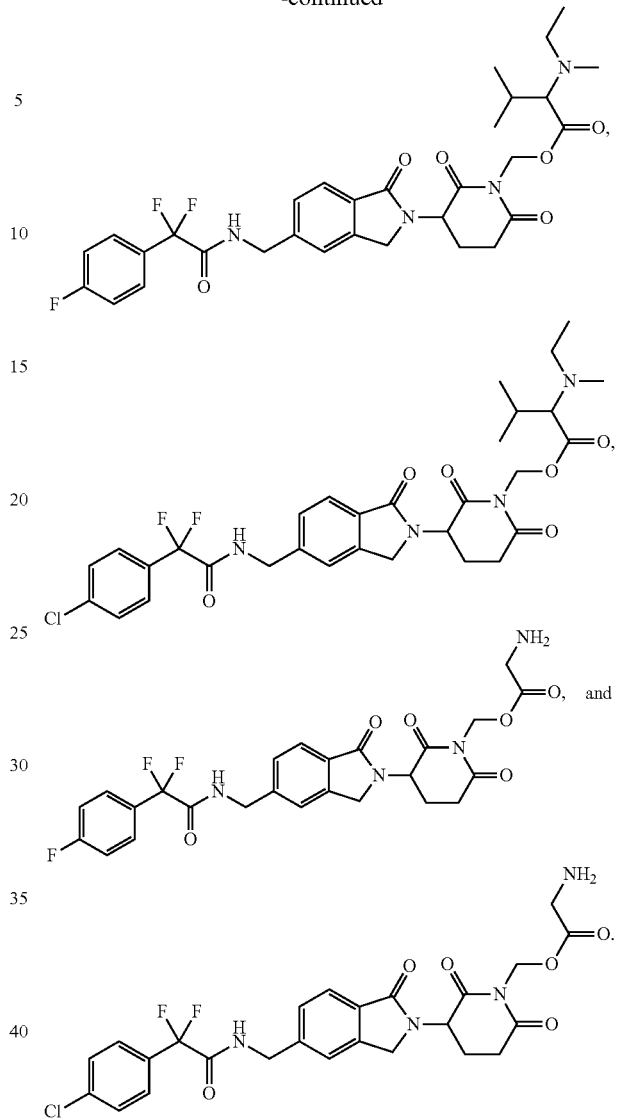

14. A pharmaceutical composition comprising a compound of claim 1 and a pharmaceutically acceptable carrier, diluent or excipient.

15. The pharmaceutical composition of claim 14, wherein the composition is formulated for parenteral, or intravenous administration.

16. The pharmaceutical composition of claim 14, wherein the composition is formulated as a single unit dosage form.

17. A pharmaceutical composition comprising a compound of claim 8 and a pharmaceutically acceptable carrier, diluent or excipient.

18. The pharmaceutical composition of claim 17, wherein the composition is formulated for parenteral, or intravenous administration.

19. The pharmaceutical composition of claim 17, wherein the composition is formulated as a single unit dosage form.

20. A method of treating cancer comprising administering to a mammal having cancer a therapeutically effective amount of the compound of claim 1.

21. The method of claim 20, wherein the cancer is leukemia.

22. The method of claim 21, wherein the leukemia is chronic lymphocytic leukemia, chronic myelocytic leukemia, acute lymphoblastic leukemia or acute myeloid leukemia.

23. The method of claim 21, wherein the leukemia is an acute myeloid leukemia.

24. The method of claim 21, wherein the leukemia is relapsed, refractory or resistant to surgery, radiation therapy, chemotherapy or hormonal therapy.

25. The method of claim 20 further comprising administering a therapeutically effective amount of a second active agent or a support care therapy.

26. The method of claim 25, wherein the second active agent is a therapeutic antibody that specifically binds to a cancer antigen, hematopoietic growth factor, cytokine, anti-cancer agent, antibiotic, cox-2 inhibitor, immunomodulatory agent, immunosuppressive agent, corticosteroid or a pharmacologically active mutant thereof.

27. A method of treating cancer comprising administering to a mammal having cancer a therapeutically effective amount of the compound of claim 8.

28. The method of claim 27, wherein the cancer is leukemia.

29. The method of claim 28, wherein the leukemia is chronic lymphocytic leukemia, chronic myelocytic leukemia, acute lymphoblastic leukemia or acute myeloid leukemia.

30. The method of claim 28, wherein the leukemia is an acute myeloid leukemia.

31. The method of claim 28, wherein the leukemia is relapsed, refractory or resistant to surgery, radiation therapy, chemotherapy or hormonal therapy.

32. The method of claim 27 further comprising administering a therapeutically effective amount of a second active agent or a support care therapy.

33. The method of claim 32, wherein the second active agent is a therapeutic antibody that specifically binds to a cancer antigen, hematopoietic growth factor, cytokine, anti-cancer agent, antibiotic, cox-2 inhibitor, immunomodulatory agent, immunosuppressive agent, corticosteroid or a pharmacologically active mutant thereof.

* * * * *